United States Patent
Xu et al.

(10) Patent No.: US 11,932,872 B2
(45) Date of Patent: Mar. 19, 2024

(54) DUAL CHIMERIC ANTIGEN RECEPTOR-T CELL WHICH CAN BE REGULATED, CONSTRUCTION METHOD THEREFOR AND USE THEREOF

(71) Applicant: NANJING ANJI BIOLOGICAL TECHNOLOGY CO., LTD, Nanjing (CN)

(72) Inventors: Hanmei Xu, Nanjing (CN); Erhao Zhang, Nanjing (CN)

(73) Assignee: NANJING ANJI BIOLOGICAL TECHNOLOGY CO., LTD, Nanjing (CN)

( * ) Notice: Subject to any disclaimer, the term of this patent is extended or adjusted under 35 U.S.C. 154(b) by 766 days.

(21) Appl. No.: 16/650,385

(22) PCT Filed: Sep. 7, 2018

(86) PCT No.: PCT/CN2018/104579
§ 371 (c)(1),
(2) Date: Mar. 25, 2020

(87) PCT Pub. No.: WO2019/062518
PCT Pub. Date: Apr. 4, 2019

(65) Prior Publication Data
US 2020/0224162 A1 Jul. 16, 2020

(30) Foreign Application Priority Data
Sep. 26, 2017 (CN) .......................... 201710884203.5

(51) Int. Cl.
| | | |
|---|---|---|
| *C12N 5/0783* | (2010.01) | |
| *C07K 14/705* | (2006.01) | |
| *C07K 14/725* | (2006.01) | |
| *C07K 16/18* | (2006.01) | |
| *C07K 16/44* | (2006.01) | |

(52) U.S. Cl.
CPC ........ *C12N 5/0636* (2013.01); *C07K 14/7051* (2013.01); *C07K 14/70521* (2013.01); *C07K 16/18* (2013.01); *C07K 16/44* (2013.01); *C07K 2317/24* (2013.01); *C07K 2317/524* (2013.01); *C07K 2317/526* (2013.01); *C07K 2317/53* (2013.01); *C07K 2317/622* (2013.01); *C07K 2319/03* (2013.01); *C07K 2319/033* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 10,105,391 B2 * | 10/2018 | Wu | ......................... | A61P 37/04 |
| 2014/0099309 A1 * | 4/2014 | Powell, Jr. | .............. | A61P 35/00 |
| | | | | 435/328 |

FOREIGN PATENT DOCUMENTS

| | | | | |
|---|---|---|---|---|
| CN | 1830487 Y | 9/2006 | | |
| CN | 105026429 A | 11/2015 | | |
| CN | 105814083 A | 7/2016 | | |
| CN | 106459989 A | 2/2017 | | |
| CN | 106755023 Y | 5/2017 | | |
| WO | WO 2014127261 Y | 8/2014 | | |
| WO | WO-2017143094 A1 * | 8/2017 | ............. | A61K 35/17 |
| WO | WO-2021146620 A2 * | 7/2021 | ......... | A61K 39/0005 |

OTHER PUBLICATIONS

Lanitis, Evripidis, et al. "Chimeric Antigen Receptor T Cells with Dissociated Signaling Domains Exhibit Focused Antitumor Activity with Reduced Potential for Toxicity in VivoTrans-Signaling CAR-T Cells for Focused Tumor Targeting." Cancer immunology research 1.1 (2013): 43-53. (Year: 2013).*
Xu, Xuequn et al. Human vaccines & immunotherapeutics vol. 13,7 (2017): 1548-1555 (Year: 2017).*
Kumar, Awanish, and Dharm Pal. Res. J. Appl. Sci. Eng. Tech 1 (2016): 42-46 (Year: 2016).*
Adamus, Tomasz, et al. Acta Biochimica Polonica 61.4 (2014) (Year: 2014).*
Janeway, Charles A. "Immunobiology: The Immune System in Health and Disease." 2001 (Year: 2001).*
Stryer, Biochemistry 4th, WH Freeman, New York. 1995 (Year: 1995).*
Colman, Research in Immunology 145.1 (1994): 33-36 (Year: 1994).*
Kim, Min Soo, et al. "Redirection of genetically engineered CAR-T cells using bifunctional small molecules." Journal of the American Chemical Society 137.8 (2015): 2832-2835. (Year: 2015).*
Zhang, E.H. et al. "A New Insight in Chimeric Antigen Receptor-Engineered T Cells for Cancer Immunotherapy" Journal of Hematology & Oncology., vol. 10, No. (1), Jan. 3, 2017 (Jan. 3, 2017), p. 1-11.

(Continued)

*Primary Examiner* — Michael Szperka
*Assistant Examiner* — Lia E Taylor
(74) *Attorney, Agent, or Firm* — Shen Huang

(57) ABSTRACT

The present invention discloses a novel switchable dual chimeric antigen receptor-T (sdCAR-T) cell and a construction method and use thereof, which fall within the field of cellular immunotherapy for tumors. The dual chimeric antigen receptor consists of a first chimeric antigen receptor for MSLN and a second chimeric antigen receptor for FITC. A dual-targeted functional T cells regulated by specific exogenous bifunctional molecules is constructed, and the exogenous molecules are used to preliminarily discuss the in vivo and in vitro activity of the dual chimeric antigen receptor-T cell. By means of in vitro and in vivo tests, it is confirmed that the activation mode of the constructed CAR-T cell is controlled by the combination of endogenous tumor antigens and exogenous bifunctional molecules, and this combined regulation mode can significantly improve the safe application of CAR-T cell immunotherapy.

3 Claims, 12 Drawing Sheets
Specification includes a Sequence Listing.

(56) References Cited

OTHER PUBLICATIONS

Zhang, E.H. et al. "Accurate Control of Dual-Receptor Engineered T Cell Activity through a Bifunctional Anti-Angiogenic Peptide." Journal of Hematology & Oncology., vol. 11, No. (44), Mar. 20, 2018 (Mar. 20, 2018), pp. 1-14.

\* cited by examiner

SEQUENCE LISTING

<160> NUMBER OF SEQ ID NOS: 18

<210> SEQ ID NO 1
<211> LENGTH: 3911
<212> TYPE: DNA
<213> ORGANISM: Artificial Sequence
<220> FEATURE:
<223> OTHER INFORMATION: synthetic sequence

<400> SEQUENCE: 1

```
gccaccatgg ccttaccagt gaccgccttg ctcctgccgc tggccttgct gctccacgcc      60
gccaggccgg gatcccaggt acaactgcag cagtctgggc ctgagctgga gaagcctggc     120
gcttcagtga agatatcctg caaggcttct ggttactcat tcactggcta caccatgaac     180
tgggtgaagc agagccatgg aaagagcctt gagtggattg gacttattac tccttacaat     240
ggtgcttcta gctacaacca gaagttcagg ggcaaggcca cattaactgt agacaagtca     300
tccagcacag cctacatgga cctcctcagt ctgacatctg aagactctgc agtctatttc     360
tgtgcaaggg ggggttacga cgggaggggt tttgactact ggggccaagg accacggtc      420
accgtctcct caggtggagg cggttcaggc ggcggtggct ctagcggtgg tggatcggac     480
atcgagctca ctcagtctcc agcaatcatg tctgcatctc aggggagaa ggtcaccatg      540
acctgcagtg ccagctcaag tgtaagttac atgcactggt accagcagaa gtcaggcacc     600
tcccccaaaa gatggattta tgacacatcc aaactggctt ctggagtccc aggtcgcttc     660
agtggcagtg gtctggaaa ctcttactct ctcacaatca gcagcgtgga ggctgaagat      720
gatgcaactt attactgcca gcagtggagt aagcaccctc tcacgtacgg tgctgggaca     780
aagttggaaa tcaaaagcag caccactacc ccagcaccga ggccacccac cccggctcct     840
accatcgcct cccagcctct gtccctgcgt ccggaggcat gtagaccgc agctggtggg      900
gccgtgcata cccggggtct tgacttcgcc tgcgatatct catttggcc cctctggct      960
ggtacttgcg gggtcctgct gctttcactc gtgatcactc tttactgtaa gcgcggtcgg    1020
aagaagctgc tgtacatctt taagcaaccc ttcatgaggc ctgtgcagac tactcaagag    1080
gaggacggct gttcatgccg gttcccagag gaggaggaag gcggctgcga actgtaagaa    1140
ttctgcagat atccgcccct ctccctcccc ccccctaac gttactggcc gaagccgctt     1200
ggaataaggc cggtgtgcgt ttgtctatat gttatttcc accatattgc cgtcttttgg    1260
caatgtgagg gccggaaac ctggccctgt cttcttgacg agcattccta ggggtctttc     1320
ccctctcgcc aaaggaatgc aaggtctgtt gaatgtcgtg aaggaagcag ttcctctgga    1380
agcttcttga agacaaacaa cgtctgtagc gaccctttgc aggcagcgga accccccacc    1440
tggcgacagg tgcctctgcg gccaaaagcc acgtgtataa gatacacctg caaaggcggc    1500
acaaccccag tgccacgttg tgagttggat agttgtggaa agagtcaaat ggctctcctc    1560
aagcgtattc aacaaggggc tgaaggatgc ccagaaggta ccccattgta tgggatctga    1620
tctggggcct cggtgcacat gctttacatg tgtttagtcg aggttaaaaa aacgtctagg    1680
ccccccgaac cacggggacg tggttttcct ttgaaaaaca cgatgataag cttgccacaa    1740
cccacaagga gacgaccttc cgcggccgca tggccctccc tgtcaccgcc tgctgcttc     1800
cgctggctct tctgctccac gccgctcggc cgctagcga cgtcgttatg actcaaaaca     1860
cactatcact tcctgttagt ctaggtgatc aagcctccat ctcttgcaga tctagtcaga    1920
gcctcgtaca cagtaatgga aacacctatt acgttggta cctgcagaag ccaggccagt     1980
ctccaaaggt cctgatctac aaagtttcca accgagtttc tggggtccca gacaggttca    2040
```

-continued

| | |
|---|---|
| gtggcagtgg atcagggaca gatttcacac tcaagatcaa cagagtggag gctgaggatc | 2100 |
| tgggagttta tttctgctct caaagtacac atgttccgtg gacgttcggt ggaggcacca | 2160 |
| agcttgaaat taagtcctct gctgatgatg ctaagaagga tgctgctaag aaggatgatg | 2220 |
| ctaagaaaga tgatgctaag aaagatggtg gcgtcaaact ggatgagact ggaggaggct | 2280 |
| tggtgcaacc tgggggggcc atgaaactct cctgtgttac ctctggattc acttttggtc | 2340 |
| actactggat gaactgggtc cgccagtctc cagagaaagg actggagtgg gtagcacaat | 2400 |
| ttagaaacaa accttataat tatgaaacat attattcaga ttctgtgaaa ggcagattca | 2460 |
| ccatctcaag agatgattcc aaaagtagtg tctatctgca aatgaacaac ttaagagttg | 2520 |
| aagacacggg tatctattac tgtacgggtg cttcctatgg tatggaatac ttgggtcaag | 2580 |
| gaacctcagt caccgtctcc accactaccc agcaccgag gccacccacc ccggctccta | 2640 |
| ccatcgcctc ccagcctctg tccctgcgtc cggaggcatg tagacccgca gctggtgggg | 2700 |
| ccgtgcatac ccggggtctt gacttcgcct gcgatatcta catttgggcc cctctggctg | 2760 |
| gtacttgcgg ggtcctgctg cttttcactcg tgatcactct ttactgtcgc gtgaaattca | 2820 |
| gccgcagcgc agatgctcca gcctaccagc aggggcagaa ccagctctac aacgaactca | 2880 |
| atcttggtcg gagagaggag tacgacgtgc tggacaagcg gagaggacgg gacccagaaa | 2940 |
| tgggcgggaa gccgcgcaga aagaatcccc aagagggcct gtacaacgag ctccaaaagg | 3000 |
| ataagatggc agaagcctat agcgagattg gtatgaaagg ggaacgcaga agaggcaaag | 3060 |
| gccacgacgg actgtaccag ggactcagca ccgccaccaa ggacacctat gacgctcttc | 3120 |
| acatgcaggc cctgccgcct cggggaagcg agctactaa cttcagcctg ctgaagcagg | 3180 |
| ctggagacgt ggaggagaac cctggaccta tgagcgagct gattaaggag aacatgcaca | 3240 |
| tgaagctgta catggagggc accgtggaca accatcactt caagtgcaca tccgagggcg | 3300 |
| aaggcaagcc ctacgagggc acccagacca tgagaatcaa ggtggtcgag ggcggccctc | 3360 |
| tccccttcgc cttcgacatc ctggctacta gcttcctcta cggcagcaag accttcatca | 3420 |
| accacaccca gggcatcccc gacttcttca agcagtcctt ccctgagggc ttcacatggg | 3480 |
| agagagtcac cacatacgaa gacgggggcg tgctgaccgc tacccaggac accagcctcc | 3540 |
| aggacggctg cctcatctac aacgtcaaga tcagaggggt gaacttcaca tccaacggcc | 3600 |
| ctgtgatgca gaagaaaaca ctcggctggg aggccttcac cgagacgctg taccccgctg | 3660 |
| acggcggcct ggaaggcaga aacgacatgg ccctgaagct cgtgggcggg agccatctga | 3720 |
| tcgcaaacat caagaccaca tatagatcca gaaacccgc taagaacctc aagatgcctg | 3780 |
| gcgtctacta tgtggactac agactggaaa gaatcaagga ggccaacaac gaaacatacg | 3840 |
| tcgagcagca cgaggtggca gtggccagat actgcgacct ccctagcaaa ctggggcaca | 3900 |
| agcttaatta a | 3911 |

<210> SEQ ID NO 2
<211> LENGTH: 6
<212> TYPE: DNA
<213> ORGANISM: Artificial Sequence
<220> FEATURE:
<223> OTHER INFORMATION: synthetic sequence

<400> SEQUENCE: 2

| | |
|---|---|
| gccacc | 6 |

<210> SEQ ID NO 3

<211> LENGTH: 608
<212> TYPE: DNA
<213> ORGANISM: Artificial Sequence
<220> FEATURE:
<223> OTHER INFORMATION: synthetic sequence

<400> SEQUENCE: 3

```
cgccctctc cctcccccc ccctaacgtt actggccgaa gccgcttgga ataaggccgg      60
tgtgcgtttg tctatatgtt attttccacc atattgccgt cttttggcaa tgtgagggcc    120
cggaaacctg gccctgtctt cttgacgagc attcctaggg gtctttcccc tctcgccaaa    180
ggaatgcaag gtctgttgaa tgtcgtgaag gaagcagttc ctctggaagc ttcttgaaga    240
caaacaacgt ctgtagcgac cctttgcagg cagcggaacc ccccacctgg cgacaggtgc    300
ctctgcggcc aaaagccacg tgtataagat acacctgcaa aggcggcaca acccccagtgc   360
cacgttgtga gttggatagt tgtggaaaga gtcaaatggc tctcctcaag cgtattcaac    420
aaggggctga aggatgccca gaaggtaccc cattgtatgg gatctgatct ggggcctcgg    480
tgcacatgct ttacatgtgt ttagtcgagg ttaaaaaaac gtctaggccc cccgaaccac    540
ggggacgtgg ttttcctttg aaaaacacga tgataagctt gccacaaccc acaaggagac    600
gaccttcc                                                              608
```

<210> SEQ ID NO 4
<211> LENGTH: 233
<212> TYPE: PRT
<213> ORGANISM: Artificial Sequence
<220> FEATURE:
<223> OTHER INFORMATION: synthetic sequence

<400> SEQUENCE: 4

```
Met Ser Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Thr Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ile Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asn Glu
        195                 200                 205
```

```
Thr Tyr Val Glu Gln His Glu Val Ala Val Ala Arg Tyr Cys Asp Leu
            210                 215                 220
Pro Ser Lys Leu Gly His Lys Leu Asn
225                 230

<210> SEQ ID NO 5
<211> LENGTH: 19
<212> TYPE: PRT
<213> ORGANISM: Artificial Sequence
<220> FEATURE:
<223> OTHER INFORMATION: synthetic sequence

<400> SEQUENCE: 5

Ala Thr Asn Phe Ser Leu Leu Lys Gln Ala Gly Asp Val Glu Glu Asn
1               5                   10                  15
Pro Gly Pro

<210> SEQ ID NO 6
<211> LENGTH: 244
<212> TYPE: PRT
<213> ORGANISM: Artificial Sequence
<220> FEATURE:
<223> OTHER INFORMATION: synthetic sequence

<400> SEQUENCE: 6

Gly Ser Gln Val Gln Leu Gln Gln Ser Gly Pro Glu Leu Glu Lys Pro
1               5                   10                  15

Gly Ala Ser Val Lys Ile Ser Cys Lys Ala Ser Gly Tyr Ser Phe Thr
            20                  25                  30

Gly Tyr Thr Met Asn Trp Val Lys Gln Ser His Gly Lys Ser Leu Glu
        35                  40                  45

Trp Ile Gly Leu Ile Thr Pro Tyr Asn Gly Ala Ser Ser Tyr Asn Gln
    50                  55                  60

Lys Phe Arg Gly Lys Ala Thr Leu Thr Val Asp Lys Ser Ser Ser Thr
65                  70                  75                  80

Ala Tyr Met Asp Leu Leu Ser Leu Thr Ser Glu Asp Ser Ala Val Tyr
                85                  90                  95

Phe Cys Ala Arg Gly Gly Tyr Asp Gly Arg Gly Phe Asp Tyr Trp Gly
            100                 105                 110

Gln Gly Thr Thr Val Thr Val Ser Ser Gly Gly Gly Gly Ser Gly Gly
        115                 120                 125

Gly Gly Ser Ser Gly Gly Ser Asp Ile Glu Leu Thr Gln Ser Pro
        130                 135                 140

Ala Ile Met Ser Ala Ser Pro Gly Glu Lys Val Thr Met Thr Cys Ser
145                 150                 155                 160

Ala Ser Ser Ser Val Ser Tyr Met His Trp Tyr Gln Gln Lys Ser Gly
                165                 170                 175

Thr Ser Pro Lys Arg Trp Ile Tyr Asp Thr Ser Lys Leu Ala Ser Gly
            180                 185                 190

Val Pro Gly Arg Phe Ser Gly Ser Gly Ser Gly Asn Ser Tyr Ser Leu
        195                 200                 205

Thr Ile Ser Ser Val Glu Ala Glu Asp Ala Thr Tyr Tyr Cys Gln
    210                 215                 220

Gln Trp Ser Lys His Pro Leu Thr Tyr Gly Ala Gly Thr Lys Leu Glu
225                 230                 235                 240

Ile Lys Ser Ser
```

```
<210> SEQ ID NO 7
<211> LENGTH: 42
<212> TYPE: PRT
<213> ORGANISM: Artificial Sequence
<220> FEATURE:
<223> OTHER INFORMATION: synthetic sequence

<400> SEQUENCE: 7

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 8
<211> LENGTH: 21
<212> TYPE: PRT
<213> ORGANISM: Artificial Sequence
<220> FEATURE:
<223> OTHER INFORMATION: synthetic sequence

<400> SEQUENCE: 8

Met Ala Leu Pro Val Thr Ala Leu Leu Leu Pro Leu Ala Leu Leu Leu
1               5                   10                  15

His Ala Ala Arg Pro
            20

<210> SEQ ID NO 9
<211> LENGTH: 256
<212> TYPE: PRT
<213> ORGANISM: Artificial Sequence
<220> FEATURE:
<223> OTHER INFORMATION: synthetic sequence

<400> SEQUENCE: 9

Ala Ser Asp Val Val Met Thr Gln Thr Pro Leu Ser Leu Pro Val Ser
1               5                   10                  15

Leu Gly Asp Gln Ala Ser Ile Ser Cys Arg Ser Ser Gln Ser Leu Val
            20                  25                  30

His Ser Asn Gly Asn Thr Tyr Leu Arg Trp Tyr Leu Gln Lys Pro Gly
        35                  40                  45

Gln Ser Pro Lys Val Leu Ile Tyr Lys Val Ser Asn Arg Val Ser Gly
    50                  55                  60

Val Pro Asp Arg Phe Ser Gly Ser Gly Ser Gly Thr Asp Phe Thr Leu
65                  70                  75                  80

Lys Ile Asn Arg Val Glu Ala Glu Asp Leu Gly Val Tyr Phe Cys Ser
                85                  90                  95

Gln Ser Thr His Val Pro Trp Thr Phe Gly Gly Gly Thr Lys Leu Glu
            100                 105                 110

Ile Lys Ser Ser Ala Asp Asp Ala Lys Lys Asp Ala Ala Lys Lys Asp
        115                 120                 125

Asp Ala Lys Lys Asp Asp Ala Lys Lys Asp Gly Val Lys Leu Asp
    130                 135                 140

Glu Thr Gly Gly Gly Leu Val Gln Pro Gly Gly Ala Met Lys Leu Ser
145                 150                 155                 160

Cys Val Thr Ser Gly Phe Thr Phe Gly His Tyr Trp Met Asn Trp Val
                165                 170                 175

Arg Gln Ser Pro Glu Lys Gly Leu Glu Trp Val Ala Gln Phe Arg Asn
            180                 185                 190
```

```
Lys Pro Tyr Asn Tyr Glu Thr Tyr Tyr Ser Asp Ser Val Lys Gly Arg
            195                 200                 205

Phe Thr Ile Ser Arg Asp Asp Ser Lys Ser Ser Val Tyr Leu Gln Met
        210                 215                 220

Asn Asn Leu Arg Val Glu Asp Thr Gly Ile Tyr Tyr Cys Thr Gly Ala
225                 230                 235                 240

Ser Tyr Gly Met Glu Tyr Leu Gly Gln Gly Thr Ser Val Thr Val Ser
            245                 250                 255

<210> SEQ ID NO 10
<211> LENGTH: 112
<212> TYPE: PRT
<213> ORGANISM: Artificial Sequence
<220> FEATURE:
<223> OTHER INFORMATION: synthetic sequence

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110

<210> SEQ ID NO 11
<211> LENGTH: 21
<212> TYPE: PRT
<213> ORGANISM: Artificial Sequence
<220> FEATURE:
<223> OTHER INFORMATION: synthetic sequence

<400> SEQUENCE: 11

Met Ala Leu Pro Val Thr Ala Leu Leu Leu Pro Leu Ala Leu Leu Leu
1               5                   10                  15

His Ala Ala Arg Pro
            20

<210> SEQ ID NO 12
<211> LENGTH: 45
<212> TYPE: PRT
<213> ORGANISM: Artificial Sequence
<220> FEATURE:
<223> OTHER INFORMATION: synthetic sequence

<400> SEQUENCE: 12

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45
```

```
<210> SEQ ID NO 13
<211> LENGTH: 24
<212> TYPE: PRT
<213> ORGANISM: Artificial Sequence
<220> FEATURE:
<223> OTHER INFORMATION: synthetic sequence

<400> SEQUENCE: 13

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 14
<211> LENGTH: 15
<212> TYPE: PRT
<213> ORGANISM: Artificial Sequence
<220> FEATURE:
<223> OTHER INFORMATION: synthetic sequence

<400> SEQUENCE: 14

Gly Gly Gly Gly Ser Gly Gly Gly Ser Ser Gly Gly Gly Ser
1               5                   10                  15

<210> SEQ ID NO 15
<211> LENGTH: 11
<212> TYPE: PRT
<213> ORGANISM: Artificial Sequence
<220> FEATURE:
<223> OTHER INFORMATION: synthetic sequence

<400> SEQUENCE: 15

Ile Val Arg Arg Ala Asp Arg Ala Ala Val Pro
1               5                   10

<210> SEQ ID NO 16
<211> LENGTH: 19
<212> TYPE: PRT
<213> ORGANISM: Artificial Sequence
<220> FEATURE:
<223> OTHER INFORMATION: synthetic sequence

<400> SEQUENCE: 16

Thr Ala Ala Thr Ala Cys Gly Ala Cys Thr Cys Ala Cys Thr Ala Thr
1               5                   10                  15

Ala Gly Gly

<210> SEQ ID NO 17
<211> LENGTH: 17
<212> TYPE: PRT
<213> ORGANISM: Artificial Sequence
<220> FEATURE:
<223> OTHER INFORMATION: synthetic sequence

<400> SEQUENCE: 17

Cys Ala Gly Gly Ala Ala Ala Cys Ala Gly Cys Thr Ala Thr Gly Ala
1               5                   10                  15

Cys

<210> SEQ ID NO 18
<211> LENGTH: 18
<212> TYPE: PRT
<213> ORGANISM: Artificial Sequence
<220> FEATURE:
<223> OTHER INFORMATION: synthetic sequence
```

```
<400> SEQUENCE: 18

Ile Val Arg Arg Ala Asp Arg Ala Ala Val Pro Gly Gly Gly Gly Arg
1               5                   10                  15

Gly Asp
```

DUAL CHIMERIC ANTIGEN RECEPTOR-T CELL WHICH CAN BE REGULATED, CONSTRUCTION METHOD THEREFOR AND USE THEREOF

TECHNICAL FIELD

The present invention belongs to the field of cellular immunotherapy for tumors, and more specifically, relates to a switchable dual-receptor CAR-T (sdCAR-T) cell, construction method and use thereof.

BACKGROUND

Biological therapy for tumors is regarded as the fourth therapeutic means following surgery, chemotherapy and radiotherapy. Adoptive cellular immunotherapy (ACI) for tumors, as one of tumor biotherapy methods, is considered to be the most promising therapeutic method. The adoptive cell therapy not only can directly kill tumor cells, but more importantly, it can improve the immune system to exert anti-tumor effect. Up to now, there are mainly six tumor cell therapies, namely lymphokine activated killer (LAK) cells, tumor infiltrating lymphocytes (TIL), cytokine induced killer (CIK) cells, dendritic cells (DCs), natural killer (NK) cells, and genetically modified T cells. As early as 1985, relevant American scholars first activated $CD3^+T$ cells in vitro with large doses of interleukin-2 (IL-2), and then used the cells to treat advanced tumor patients, thus opening up the field of tumor cell immunotherapy. However, this method involves the use of large doses of IL-2, which is highly toxic, and LAK has low amplification ability in vitro and low tumor killing activity in vivo, so this method gradually withdraws from clinical treatment. The subsequent TIL cell therapy has significantly higher tumor lethality than LAK and does not require the use of large-dose IL-2. However, the extraction of TIL cells is troublesome, which is the main factor limiting its application. At present, widely used cell therapies include CIK, DC, NK and genetically modified T cells. CIK is a non-MHC restricted immune active cell obtained by a human peripheral blood mononuclear cell (PBMC) stimulated by various cytokines in vitro. Its anti-tumor activity mainly induces apoptosis of tumor cells by releasing granzyme and perforin, releasing a large amount of regulatory cytokines and being able to bind to Fas death receptor on the surface of tumor cell membrane. DC is the largest antigen presenting cell in the body. It can effectively present soluble tumor antigen and enhance the specific immune response of the body to tumors. The mechanism of exerting anti-tumor immune response in vivo mainly includes inducing the production of a large number of effector T cells, implementing the chemotaxis of the effector T cells to tumor sites, secreting a variety of anti-tumor cytokines such as IL-12 and IL-1β, tumor necrosis factors, and the like. DC can also effectively inhibit tumor angiogenesis. NK cells are the main bearers of natural immunity in the body. Compared with T cells, the NK cells have the greatest advantages that they can kill tumor cells without identification of a tumor specific antigen. The NK cells are important effector cells for natural immunotherapy of tumors. In vivo anti-tumor activity is mainly achieved by releasing perforin, NK cytotoxic factors and tumor necrosis factors. T cells are the most important immune cells in the body and have the characteristic of "MHC restriction" when functioning. However, immune escape seriously affects the killing effect of T cells on tumor cells. Therefore, in order to improve the function of the T cells, genetic engineering methods are used to modify the T cells, so that the T cells specifically kill tumor cells. At present, there are two main forms of the modified T cells: TCR-T and CAR-T cells, among them, CAR-T is the best form. It enables the T cells can react with tumor antigens through non-MHC restricted pathways, thus breaking through the limitation of tumor antigen types and avoiding rapid growth of tumors in vivo resulting from the immune escape phenomenon. Due to its positive effect in tumor treatment, this technology was ranked as the top ten scientific breakthroughs by Science as early as 2013.

CAR-T cell therapy has good therapeutic effects on many types of tumors, especially hematological tumor and lymphoma. However, with its clinical application, this cell therapy has serious side effects, mainly including cytokine storm and normal tissue damage. Cytokine storm is caused by excessive cytokines released by CAR-T cells killing tumor cells in a short period of time. Therefore, the cytokine storm can be relieved by controlling the amount of cytokines released. At present, the activation state of T cells can be controlled through external small molecular switch, and the activation number of CAR-T cells can be implemented by the addition of small molecules with different dosages, so that the safe application of CAR-T cells can be realized. The damage of CAR-T cells to normal tissues during treatment, namely targeted non-tumor toxicity, is caused by the fact that tumor antigens targeted by the designed CAR structure are mostly tumor associated antigens (TAAs), which are expressed on tumors and normal tissues simultaneously and do not have tumor cell specificity, thus leading to the generation of "targeted non-tumor" toxicity. In order to improve the safety of CAR-T cells, there are mainly two methods: endogenous and exogenous pathways. The endogenous pathway mainly refers to the screening of receptors for tumor-specific antigens through bioinformatics means and the modification of T cells through gene recombination to enable the T cells to specifically target the tumor cells. The exogenous pathway mainly refers to controlling the active state and quantity of T cells through exogenous active small molecules.

As the most commonly used tumor marker, mesothelin (MSLN) is widely used in the detection of various tumors. It is mainly expressed in a variety of solid tumors, such as esophageal cancer, pancreatic cancer, lung cancer, ovarian cancer, colorectal cancer, gastric cancer, breast cancer, liver cancer, melanoma, head and neck cancer, cervical cancer and osteosarcoma. Its expression will greatly increase with the malignancy of the tumor, and it will also be slightly expressed in normal mesothelial cells of pleura, pericardium and peritoneum. Therefore, in clinical practice, when CAR-T cells targeting MSLN antigens are used for tumor immunotherapy, the CAR-T cells not only kill tumor cells with positive MSLN, but also cause damages to normal tissues and even endanger lives. Therefore, the improvement of the safety of CAR-T cell therapy has become a close concern of doctors and researchers.

SUMMARY

1. Problems to be Solved

In view of cytokine storm and toxicity of normal tissue damage occurring in the current chimeric antigen receptor T cell therapy, the present invention provides an sdCAR-T cell with an anti-FITC single chain antibody (FITCscFv) and an anti-MSLN single chain antibody (MSLNscFv), which is controlled by an exogenous bifunctional molecule, where downstream parts of the receptors are connected in series with CD3ζ and 4/1BB signal domains of a T cell activation signal pathway respectively, and T lymphocyte is transfected by an efficient electrotransfection mode. Preliminary studies show that the modified T cells can be completely activated only when both switching molecules and antigens are recognized, thus effectively reducing the damage to normal tissues and enhancing the safety of sdCAR-T cell therapy. FITC and polypeptide HM-3 with anti-tumor effects are further coupled to form a bifunctional specific small molecule drug. The small molecule drug can be used to increase the ability of sdCAR-T cells to target tumor cells. It can effectively control the state and activation quantity of sdCAR-T cells, and enhance the overall anti-tumor effect. In summary, the combination of endogenous and exogenous regulations can greatly alleviate the severe problems in the current CAR-T cell therapy and can also improve the effectiveness of CAR-T cell therapy, and its application in clinical therapy is further explored.

2. Technical Solution

In order to solve the foregoing problems, the technical solutions adopted by the present invention are as follows:

A switchable dual chimeric antigen receptor is provided, wherein the dual chimeric antigen receptor consists of a first chimeric antigen receptor for MSLN and a second chimeric antigen receptor for FITC.

Further, the first chimeric antigen receptor includes a light chain and heavy chain variable region MSLNscFv of MSLN monoclonal antibody and a signaling domain, wherein the signaling domain is composed of a hinge region, a transmembrane region and an intracellular signal domain in series.

Further, the hinge region of the first chimeric antigen receptor is CH2-CH3 sequence of IgG1 or a human CD8α hinge region, the transmembrane region is a human CD3 transmembrane region or a human CD8 transmembrane region or a human CD28 transmembrane region, and the intracellular signal domain is a human 4/1BB costimulatory signal domain.

Further, the amino terminal of the first chimeric antigen receptor contains a secretory signal peptide.

Further, the light chain and heavy chain variable region MSLNscFv of the MSLN monoclonal antibody includes a linker between light chain and heavy chain, and the linker can be different amino acid sequences, and is preferably Gly Gly Gly Gly Ser Gly Gly Gly Gly Ser Ser Gly Gly Gly Ser (SEQ ID NO. 14) linker peptide.

Further, the amino acid sequence of the secretory signal peptide is shown in SEQ ID NO. 8 in SEQUENCE LISTING.

Further, the amino acid sequence of the light chain and heavy chain variable region MSLNscFv of the MSLN monoclonal antibody is SEQ ID NO. 6 or a variant with 80% sequence identity thereof.

Further, the amino acid sequence of the human CD8α hinge region is shown in SEQ ID NO. 12 in SEQUENCE LISTING; the amino acid sequence of the human CD8 transmembrane region is shown in SEQ ID NO. 13 in SEQUENCE LISTING; and the amino acid sequence of the human 4/1BB costimulatory signal domain is shown in SEQ ID NO. 7 in SEQUENCE LISTING.

Further, the second chimeric antigen receptor includes a light chain and heavy chain variable region FITCscFv (SEQ ID NO. 9) of anti-FITC monoclonal antibody and a signaling domain, wherein the signaling domain is composed of a hinge region, a transmembrane region and an intracellular signal domain in series.

Further, the hinge region of the second chimeric antigen receptor is CH2-CH3 sequence of IgG1 or a human CD8α hinge region, the transmembrane region is a human CD3 transmembrane region or a human CD8 transmembrane region or a human CD28 transmembrane region, and the intracellular signal domain is an antigen recognition signal structure CD3ζ.

Further, the amino terminal of the second chimeric antigen receptor contains a secretory signal peptide.

Further, the amino acid sequence of the secretory signal peptide is shown in SEQ ID NO. 11 in SEQUENCE LISTING, and SEQ ID NO. 8 is the same as SEQ ID NO. 11.

Further, the amino acid sequence of the FITCscFv is shown in SEQ ID NO. 9 in SEQUENCE LISTING or a variant with 80% sequence identity thereof.

Further, the intracellular signal domain is an antigen recognition signal structure CD3ζ, and the amino acid sequence of which is shown in SEQ ID NO. 10 in SEQUENCE LISTING.

Further, the gene sequence of the dual chimeric antigen receptor contains a Kozak sequence upstream, and the nucleotide sequence of which is shown in SEQ ID NO. 2 in SEQUENCE LISTING.

Further, a linker sequence IRES is contained between the first chimeric antigen receptor and the second chimeric antigen receptor, and the nucleotide sequence of which is shown in SEQ ID NO. 3 in SEQUENCE LISTING.

Further, the dual chimeric antigen receptor contains a blue fluorescent protein tag downstream.

Further, the fluorescent protein tag is BFP, and its amino acid sequence is shown in SEQ ID NO. 4 in SEQUENCE LISTING.

Further, a linker peptide P2A is contained between the dual chimeric antigen receptor and the fluorescent protein tag, and the amino acid sequence of which is shown in SEQ ID NO. 5 in SEQUENCE LISTING.

Further, the nucleotide sequence of the dual chimeric antigen receptor is shown in SEQ ID NO. 1.

A method for preparing a switchable dual-receptor CAR-T (sdCAR-T) cell capable of expressing the above dual chimeric antigen receptor by transfection is provided, wherein the dual chimeric antigen receptor gene is ligated to an overexpression vector, and the gene expressing the dual chimeric antigen receptor is inserted into genome of T lymphocyte by using a φC31 site-specific integrase system to prepare the sdCAR-T cell.

A CAR-T cell is capable of expressing the above dual chimeric antigen receptor.

A method for controlling the activity of the above sdCAR-T cell is provided, wherein activity of the sdCAR-T cell is controlled by using a molecular switch containing an FITC fragment in combination with an endogenous tumor antigen mesothelin (MSLN).

Further, the molecular switch containing an FITC fragment is FITC or a fragment obtained by coupling the FITC with a polypeptide, protein or small molecular compound.

Further, the polypeptide contains the following domains: Ile-Val-Arg-Arg-Ala-Asp-Arg-Ala-Ala-Val-Pro (SEQ ID NO. 15) and Arg-Gly-Asp.

Further, the sequence of the polypeptide is HM-3 sequence, and the amino acid sequence of the HM-3 sequence is Ile-Val-Arg-Arg-Ala-Asp-Arg-Ala-Ala-Val-Pro-Gly-Gly-Gly-Gly-Arg-Gly-Asp (SEQ ID NO. 18).

Use of the above CAR-T cell in the field of preparing tumor drugs for treating overexpression of tumor antigen MSLN and integrin αvβ3 is provided.

Further, the tumors include ovarian cancer, lung cancer, esophageal cancer, pancreatic cancer, gastric cancer, colon cancer, breast cancer, liver cancer, melanoma, head and neck cancer, cervical cancer and osteosarcoma.

Use of the above dual chimeric antigen receptor in the preparation of a medicament for treating tumor cells is provided.

A medicament for tumor cell therapy comprises the above sdCAR-T cell or the above CAR-T cell, and pharmaceutically acceptable excipients.

In the dual chimeric antigen receptor Signal peptideI-MSLNscFv-CD8α-CD8 TM-4/1BB-IRES-Signal peptideII-FITCscFv-CD8α-CD8 TM-CD3ζ-P2A-BFP of the present invention, the first chimeric antigen receptor is composed of a light chain and heavy chain variable region MSLNscFv of MSLN monoclonal antibody, a human CD8α hinge region, a human CD8 transmembrane region and an intracellular 4/1BB costimulatory signal domain structure in series; the second chimeric antigen receptor is composed of a light chain and heavy chain variable region FITCscFv of anti-FITC monoclonal antibody, a human CD8α hinge region, a human CD8 transmembrane region and an intracellular CD3ζ structure in series; the two chimeric antigen receptors each contain a secretory signal peptide upstream, which is used for guiding the formation and positioning of the CAR structure in extracellular domain proteins, and the two chimeric receptors are connected by internal ribosome entry site (IRES); and a blue protein fluorescent tag BFP is inserted in the terminal of the sequence, which can facilitate the observation of CAR-T cells and tumor cells by flow or fluorescence microscope, and is also beneficial to the studies of in vivo tests. The second chimeric antigen receptor contains a P2A sequence downstream, so that BFP fluorescent protein can be lysed by the body's own polypeptide lyase after a fusion protein is expressed. The nucleotide sequence of the sdCAR is shown in SEQ ID NO. 1.

A tumor cell MSLN$^+$K562 cell overexpressed by MSLN containing a green fluorescent protein is screened by puromycin to obtain a homologous target cell stably expressing the MSLN; and a tumor cell overexpressed by a carcionembryonic antigen (CEA) containing a red fluorescent protein is screened by hygromycin to obtain a non-homologous target cell stably expressing the CEA.

An exogenous bifunctional molecular switch FHBM is added to regulate in vivo and in vitro activity of sdCAR-T cells. The activity of the sdCAR-T cells depends on the antigen MSLN of endogenous homologous tumor cells and the exogenous switching molecules FHBM. The safety and effectiveness of tumor cell therapy can be improved by controlling the activity of CAR-T cells through both endogenous and exogenous pathways, thus promoting their application in tumor immunotherapy.

3. Beneficial Effects

Compared with the prior art, the present invention has the following beneficial effects:

(1) The present invention mainly adopts the endogenous and exogenous methods to control the activity of T cells, so that higher safety can be achieved while the T cells can exert cytotoxicity; HM-3 is a novel anti-angiogenesis polypeptide containing 18 amino acids, and designed and developed by the applicant using an Arg-Gly-Asp (RGD) modification technology in the early stage, and the applicant has been granted a national invention patent. The applicant combines an RGD sequence having integrin targeting function with an endostatin C-terminal fragment IVRRADRAAVP (SEQ ID NO. 15). Under the guidance of the RGD sequence, the targeting of endostar (ES) to integrin is strengthened and toxicity and side effects are reduced. In addition, HM-3 has both RGD and ES activities in vitro, and it can be developed into anti-tumor drugs. Research shows that the main target of HM-3 is integrin αvβ3, which has tumor targeting effect and can specifically bind to tumor endothelial cells. The applicant further uses a gene coupling technology to connect HM-3 to FITC to form a bispecific molecule, which not only retains the function of HM-3 to target integrin αvβ3 on the surface of tumor cells, but also specifically recognizes FITCscFv. That is, this bispecific small molecule can simultaneously target tumor cells expressing the integrin αvβ3 and FITCscFv-modified sdCAR-T cells, promoting the homing ability of the sdCAR-T cells, and enhancing the killing effect of the T cells on tumor cells.

(2) The present invention uses a gene recombination technology to construct sdCAR-T cells, which have the function of targeting MSLN and FITC. The FITCscFv of the dual-receptor T cell contains an antigen recognition signal domain CD3ζ downstream, and controls the state of it. And MSLNscFv contains a costimulatory signal domain 4/1BB downstream, and controls the state of it. Therefore, the state and activation dose of the sdCAR-T cell can be controlled by utilizing the coupled bifunctional small molecules of HM-3 and FITC. By using bifunctional small molecule compounds and sdCAR-T cells, the following advantages can be achieved: first, since the activation state of the sdCAR-T cells can be remotely controlled by using exogenous bifunctional small molecules, the bifunctional small molecules can be added to exert tumor killing effects when T cells mostly home around tumor cells, thus effectively reducing cytotoxicity of targeted non-tumor cells, thereby improving the safety of sdCAR-T cells and promoting clinical application thereof; second, because the small molecule can control the state of sdCAR-T cells, the quantity of the sdCAR-T cells activated can be regulated by constantly detecting the state of the body after reinfusion of sdCAR-T cells and changing the dose of added switching molecules, so that the cytokine release syndrome occurring in the body can be controlled, and the toxicity of cytokine storm can be effectively solved; third, the exogenous small molecules used can target both tumor cells and sdCAR-T cells simultaneously, thus effectively improving the homing ability of the T cells and well targeting tumor cells, and thereby enhancing the specificity and effectiveness of sdCAR-T cells; fourth, the bifunctional small molecules have the characteristics of HM-3 itself, and can achieve the anti-tumor purpose by inhibiting angiogenesis; and especially for solid tumors, the anti-tumor effect of small molecules can be combined with the function of sdCAR-T cells to kill tumor cells to enhance the overall anti-tumor effect.

(3) According to gene sequence information of MSLNscFv and FITCscFv, the present invention performs codon optimization on MSLNscFv and FITCscFv, and at the same time, sequence information on a humanized signal peptide gene, a human CD8α hinge region gene, a human CD8 transmembrane region, a human CD3ζ signal domain and a 4/1BB costimulatory signal domain gene as well as a functional peptide P2A and a tag protein BFP is retrieved from a GenBank database of the US National Center for Biotechnology Information (NCBI). Finally, a gene fragment Signal peptide I-MSLNscFv-CD8α-CD8 TM-4/1BB-IRES-Signal peptide II-FITCscFv-CD8α-CD8 TM-CD3ζ-

P2A-BFP is synthesized by a whole gene synthesis method, and cleavage sites Afl II and Xba I are selected and inserted into an overexpression vector pFC-PGK-MCS (pFC-empty vector) of a φC31 integrase system to form an sdCAR expression plasmid (pFC-sdCAR plasmid). The φC31 integrase system is used to recombine the sdCAR expression plasmid into a T cell genome to make T cells express a dual chimeric antigen receptor. Exogenous bifunctional molecules (FITC and a polypeptide HM-3 are coupled to form bifunctional small molecules FHBM) are used to regulate the activity of constructed CAR-T cells, thus enabling the T cells to have higher specificity and safety.

(4) The functional activity of the sdCAR-T cells constructed by the present invention is verified through in vitro tests and in vivo tests. The obtained sdCAR-T cells are co-cultured with modified MSLN single positive tumor cells K562 in vitro, and then the bifunctional molecule FHBM is added. The functional activity of the sdCAR-T cells is discussed by detecting the activation and tumor killing activity of the sdCAR-T cells and the toxicity of the sdCAR-T cells to tumor cells in vivo. In order to verify its specificity and safety, a group of negative control tumor cell strains, namely CEA single positive tumor cells, is designed to verify the specificity of the constructed sdCAR-T cells. Finally, it is confirmed that the constructed sdCAR-T cells are precisely activated and play a killing function through the joint regulation of the exogenous bifunctional molecule FHBM and the endogenous tumor antigen MSLN. The design of this sdCAR structure can not only effectively improve the targeting specificity of T cells, but also regulate the activation state and activation dose of sdCAR-T cells through exogenous switching molecules, thus improving the application safety. This exogenous bifunctional molecule functions as a switch for activation of sdCAR-T cells and a control knob for their activity. Therefore, finally the safe application of the CAR-T cells can be achieved and the damage to normal tissues is reduced. Therefore, the sdCAR-T cells of the present invention can achieve better therapeutic effects in tumor cell therapy by using exogenous bifunctional molecules in combination.

DETAILED DESCRIPTION

The present invention is further described below with reference to specific examples.

EXAMPLE 1

Determination of Whole Gene Sequence of a Dual Chimeric Antigen Receptor

Referring to relevant information in the NCBI database, the amino acid sequence of MSLNscFv (GenBank: AAC04760) and the amino acid sequence of FITCscFv (PDB: 1X9Q_A) were obtained. Their gene sequences were analyzed and optimized to ensure that they were more suitable for high-efficiency expression in humanized T lymphocytes without changing the coding amino acid sequence. The sequence information of MSLNscFv is detailed in SEQUENCE LISTING (SEQ ID NO. 6); and the sequence information of FITCscFv is detailed in SEQUENCE LISTING (SEQ ID NO. 9). The amino acid sequence of a humanized signal peptide (SEQ ID NO. 8 or 11 in SEQUENCE LISTING), the amino acid sequence of a humanized CD8α hinge region (SEQ ID NO. 12), the amino acid sequence of a human CD8 transmembrane region and intracellular domain gene (SEQ ID NO. 13 in SEQUENCE LISTING), the amino acid sequence of human CD3ζ (SEQ ID NO. 10 in SEQUENCE LISTING), the amino acid sequences of a 4/1BB signal domain (SEQ ID NO. 7 in SEQUENCE LISTING), the amino acid sequence of IRES (SEQ ID NO. 3 in SEQUENCE LISTING), as well as the amino acid sequence of a linker peptide P2A (SEQ ID NO. 5 in SEQUENCE LISTING) and the amino acid sequence of a blue protein tag BFP (SEQ ID NO. 4 in SEQUENCE LISTING) were retrieved from a GenBank database on the website of NCBI (http://www.ncbi.nlm.nih.gov/).

Figure 1:
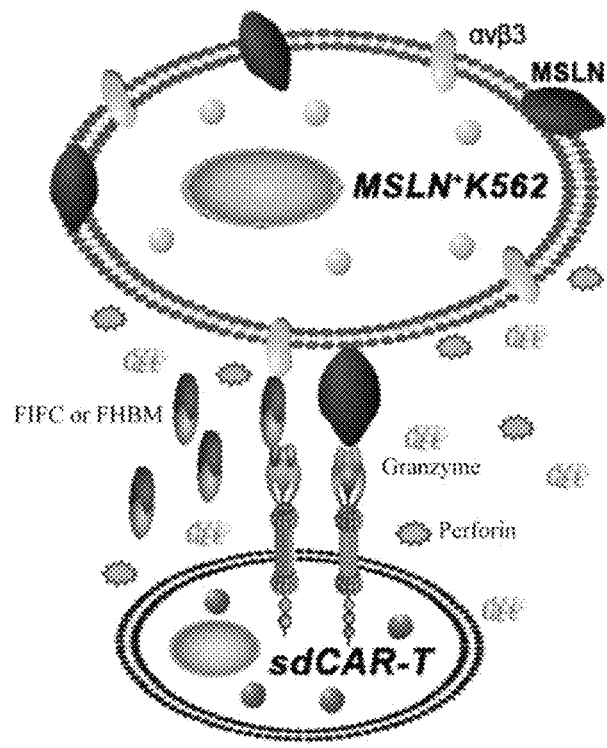
FIG. 1 is a schematic diagram showing the structure and killing mechanism of sdCAR-T cells.

The above gene sequences were sequentially connected according to the sequences of the signal peptide, MSLN-scFv, the human CD8α hinge region, the human CD8 transmembrane region and intracellular domain, the human 4/1BB costimulatory signal region, IRES, the signal peptide, FITCscFv, the human CD8α hinge region, the human CD8 transmembrane region and intracellular domain, and the human CD3ζ intracellular domain, and a Kozak sequence (SEQ ID NO. 2 in SEQUENCE LISTING) was introduced at the head end to finally construct complete gene sequence information of the sdCAR (SEQ ID NO. 1). The structure and killing mechanism of sdCAR-T cells are shown in FIG. 1.

EXAMPLE 2

Construction of an Overexpression Plasmid for a Dual Chimeric Antigen Receptor 2.1 Synthesis of a Gene Fragment An optimized complete sdCAR gene sequence was subjected to whole gene synthesis (Suzhou GENEWIZ Biotechnology Co., Ltd.) and then cloned into an overexpression vector pFC-PGK-MCS of a φC31 site-specific recombinant enzyme system through specific cleavage sites Afl II and Xba I to finally construct a recombinant plasmid pFC-sdCAR. A fluorescent tag BFP was introduced to facilitate detection and tracking of the constructed sdCAR-T cells.

2.2 Construction and Sequencing of the Recombinant Plasmid

The recombinant plasmid was sent to Suzhou GENEWIZ Biotechnology Co., Ltd. for sequencing. Sequencing results were compared with the sdCAR gene sequence to be synthesized. The results confirmed that the synthesized sequence was correct and a target gene fragment was linked to the overexpression vector pFC-PGK-MCS.

The sequencing primer used is a universal primer on pFC vector:

```
Upstream primer (5'→3'):
TAATACGACTCACTATAGG        (SEQ ID NO. 16)

Downstream primer (5'→3'):
CAGGAAACAGCTATGAC          (SEQ ID NO. 17)
```

EXAMPLE 3

Acquisition of Recombinant Tumor Cells 3.1 Design of an Overexpression Vector for MSLN Lentivirus References were made to the CDS region sequence of MSLN in the GenBank database on the NCBI website (the gene sequence number is NM_013404). There was a linker peptide P2A between MSLN and GFP. The MSLN-P2A-GFP gene fragment was inserted into a lentivirus overexpression vector pLVX through cleavage sites EcoRI and XbaI to form a pLVX-MSLN recombinant expression plasmid.

3.2 Design of an Overexpression Vector for CEA Lentivirus

References were made to the CDS region sequence of humanized MSLN CEA in the GenBank database on the NCBI website (the gene sequence number is M29540.1). There was a linker peptide P2A between CEA and mCherry. The CEA-P2A-mCherry gene fragment was inserted into a lentivirus overexpression vector pLVX through cleavage sites EcoRI and XbaI to form a pLVX-CEA recombinant expression plasmid.

3.3 Preparation of Lentivirus Particles

1) A 15 cm culture dish was prepared, and the complete culture medium (DMEM with high glucose) containing 10% fetal bovine serum (FBS) was add. $5 \times 10^6$ 293T cells were inoculated and placed in an incubator at 37° C. with 5% $CO_2$, cultured overnight.

2) The constructed overexpression vector pLVX-MSLN or pLVX-CEA (the concentration is about 100 μM) and lentivirus packaging plasmids (Lenti-GOI, pGP, and pVSVG) were taken out from a refrigerator. After thawing at room temperature, they were blown up and down with a pipette for complete and uniform mixing.

3) The phosphate buffered saline (PBS) was taken out and heated to room temperature. 2 mL of PBS was taken to a well of a 6-well plate, 10 μg of Lenti-GOI, 6 μg of pGP and 5 μg of pVSVG were add respectively. After they were blown up and down with the pipette for full mixing, 18 μL of pLVX-MSLN or pLVX-CEA was added, then immediately blown up and down with the pipette for uniform mixing, and standed for 10 min at room temperature.

4) The complex of the above overexpression plasmid pLVX-MSLN (or pLVX-CEA) and various packaging plasmids were added dropwise into 293T cells cultured overnight, and the culture dish was gently shaked for full and uniform mixing. Then the culture dish was placed in an incubator at 37° C. with 5% $CO_2$.

5) After culturing for 6-8 h (preferably 8 h in this example), the culture medium containing the transfection reagent was removed and replaced with fresh complete culture medium.

6) After continuous cultivation for 48-72 h (preferably 48 h in this example), the culture medium supernatant containing virus in the culture dish was collected.

7) The obtained culture medium supernatant was filtered with a 0.45 μm filter membrane, the filtrate was transferred to centrifuge tubes, and centrifuged at a centrifugal force of 50000 g at a high speed at 4° C. for 2 h.

8) After centrifugation, the liquid from the centrifuge tubes was carefully sucked in a biosafety cabinet, and 500 μL of PBS was added to resuspend the precipitate. The virus was stored at −80° C.

9) The titer of the obtained lentivirus particles was determined. The titer of the virus particles overexpressing the MSLN was $1.13 \times 10^8$ TU/mL, and the titer of the virus particles overexpressing the CEA was $1.62 \times 10^8$ TU/mL.

3.4 Determination of the Killing Curve of K562 Tumor Cells by Puromycin

1) Low-generation cell strains were resuscitated from liquid nitrogen, and subjected to conventional culture and passaged 5 times, then the cell state was adjusted to a logarithmic growth period.

2) A new 24-well plate was prepared, 50000 K562 tumor cells were inoculated per well for 7 wells in total, and 500 μL of complete culture medium (RPMI1640, 10% FBS) was added per well. The well plate was placed in an incubator at 37° C. with 5% $CO_2$ and cultured overnight.

3) The cell well plate was taken out from the incubator, one well was left free of puromycin, and puromycin with final concentrations of 0.5, 1, 2, 4, and 8 μg/mL were added to the remaining wells respectively.

4) The well plate was placed in an incubator at 37° C. with 5% $CO_2$ for continuous cultivation. The state of cells in the well plate was observed under a microscope every day for 5 consecutive days. And the minimum concentration that can completely kill all cells on the fifth day was taken as the puromycin concentration for subsequent stable cell strain screening.

Through the determination of the killing curve, the concentration of puromycin was finally selected to be 1 μg/mL.

3.5 Determination of a Killing Curve of K562 Tumor Cells by Hygromycin

The method is the same as that of Example 3.4. The concentration gradient of the hygromycin was set to 50, 100, 200, 400 and 800 μg/mL respectively, and the concentration of the hygromycin was finally selected to be 100 μg/mL through the determination of the killing curve.

3.6 Lentivirus Transfection Test of K562 Tumor Cells

1) Low-generation cell strains were resuscitated from liquid nitrogen, and subjected to conventional culture and passaged 5 times, then the cell state was adjusted to a logarithmic growth period.

2) A new 6-well plate was prepared, the cells were inoculated according to the density of $3\times10^5$ cells/well for a total of 2 wells and complete culture medium (RPMI1640, 10% FBS) was added to 3 mL/well. The well plate was placed in an incubator at 37° C. with 5% $CO_2$ and cultured overnight.

3) A tube of overexpressed lentivirus was taken out from the −80° C. refrigerator and placed in a 37° C. water bath for quick thawing. The cells were taken out from the incubator and replaced the culture medium with fresh complete culture medium (RPMI1640, 10% FBS).

4) Polybrene with a final concentration of 6 μg/mL was added to the culture medium in one of the wells, then 100 μL of lentivirus was added, and gently blown with the pipette for uniform mixing.

5) The well plate was placed in a horizontal centrifuge and centrifuged at a centrifugal force of 800 g for 1 h. After centrifugation, the well plate was placed in an incubator at 37° C. with 5% $CO_2$ for continuous cultivation for 24 h.

6) The well plate was taken out from the incubator, placed in the horizontal centrifuge, and centrifuged at a centrifugal force of 2000 g for 5 min, then the culture medium containing virus supernatant was removed from the well plate. Fresh culture medium (RPMI1640, 10% FBS) without antibiotics was added, and continued to culture for 2 days (if the cell density was large, passage can be carried out).

7) The well plate was taken out from the incubator, placed in the horizontal centrifuge, and centrifuged at a centrifugal force of 2000 g for 5 min, then the culture medium was removed from the well plate, and the culture medium containing puromycin or hygromycin antibiotic was added, wherein the concentrations of the puromycin and hygromycin used were the same as those selected in Example 3.4 and 3.5, respectively.

8) The control well cells not infected with virus were taken as the control and continuously cultured for 5 days until the control group cells were completely dead, so that the cells surviving in the well infected with virus were the stable cell strains successfully constructed.

Figure 3:
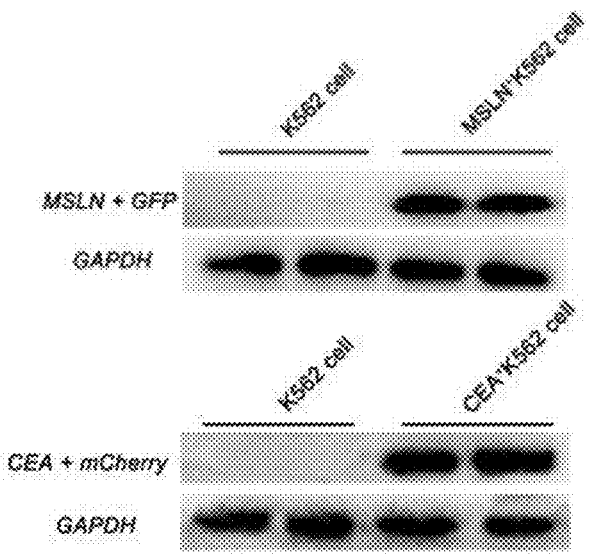
FIG. 3 is a diagram showing Western Blot analysis of MSLN and CEA expression after transfection of K562 cell.

9) Western Blot was used to detect the expression of target genes in the stable cell strains, as shown in FIG. 3.

3.7 Expression of Integrins αv and β3 in K562 Tumor Cells

Figure 4:
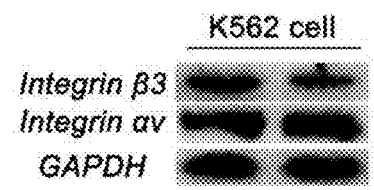
FIG. 4 is a diagram showing Western Blot analysis of integrin αvβ3 expression in K562 cells.

Western Blot was used to detect the expression of integrin αvβ3 in K562 cell strains, as shown in FIG. 4. The results showed that K562 cells highly expressed integrin αvβ3.

EXAMPLE 4

Preparation of T Lymphocytes in Peripheral Blood 4.1 Acquisition of PBMC

The PBMC includes lymphocytes, monocytes and the like. Their volume, morphology and density are different from those of other cells. The cell densities of red blood cells and granulocytes and the like are larger, about 1.092 g/mL, while the densities of the lymphocytes and monocytes are about 1.070 g/mL. Ficoll reagent, a lymphocyte separation solution, was a mixture of 60% polysucrose and 34% meglumine diatrizoate at a ratio of 2:1, with a specific weight of about 1.077±0.001. The lymphocytes were separated from other blood cells by centrifugation and distribution according to density gradient. The specific implementation method includes the following steps of: taking 1 mL of fresh anticoagulant and PBS and evenly mixing at a ratio of 1:1, carefully adding 1 mL of Ficoll separation solution, and centrifuging at 2000 rpm for 20 min at room temperature, at this time the cells in a centrifuge tube are divided into four layers from bottom to top; collecting an upper second milky film layer as PBMC layer; after fully and evenly mixing the PBMC with 5 mL of PBS, centrifuging at 1000 rpm for 10 min, and washing twice to obtain the PBMC with relatively high purity.

Figure 5:
FIG. 5 is a diagram showing the state of an isolated humanized PBMC.

The PBMC obtained by separation was inoculated into a 15 cm culture dish at a cell density of $5\times10^5$ cells per ml, the culture medium was RPMI1640 containing 10% FBS, and cytokine IL-2 with a final concentration of 50 U/mL was added. The culture dish was placed in an incubator at 37° C. with 5% $CO_2$ for 48 h, and the cell state was observed under a microscope after the culture was completed. The results are shown in FIG. 5. It can be observed that the cell state had obvious differentiation after PBMC culture. Some of the cells were round and transparent suspension cells growing in an aggregated manner, while some other cells are cells that began to adhere to the wall and grew in a spindle shape. After analysis, the cells growing in suspension should be lymphocytes and the cells with adherent growth should be monocytes.

4.2 Magnetic-Activated Cell Sorting of T Cells

Figure 6:
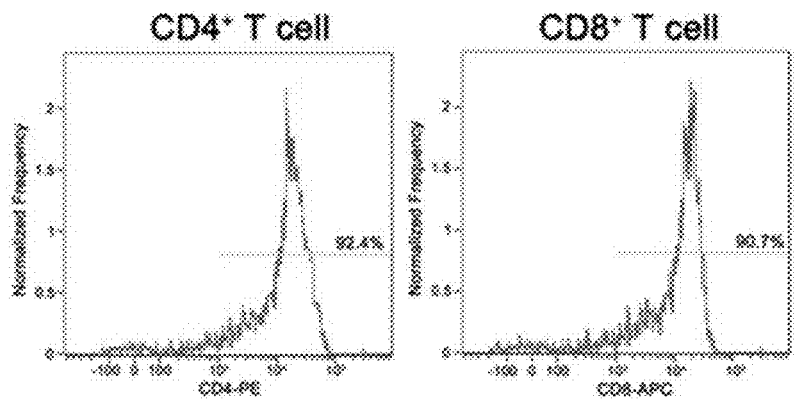
FIG. 6 is a flow cytometry diagram of CD4$^+$T cells and CD8$^+$T cells.

This example mainly used the magnetic-activated cell sorting method to obtain target T cells. Immunomagnetic bead sorting is based on the antigen expressed on the cell surface and the microbeads coupled to the antibody corresponding to the antigen. After the antigen is incubated with the antibody, an external magnetic field is added, and the microbeads attached to the antibody remain in the magnetic field under the action of a strong magnetic field. Therefore, only cells expressing the antigen remain in the magnetic field, thus realizing separation of target cells. At present, immunomagnetic bead sorting methods mainly include positive sorting method, negative sorting method and compound sorting method. The positive sorting method means that the cells bound by microbeads are target cells; the negative sorting method means that the cells bound by microbeads are not target cells. The compound sorting method means removing non-targeted cells by using the negative sorting method and then using the positive sorting method. This method is mainly used to sort cell populations with a low content. According to the present invention, $CD4^+T$ cells and $CD8^+T$ cells were sorted by using the positive sorting method, and the sorting result was subjected to flow cytometry. The results are shown in FIG. 6. The results showed that the positive rates of the $CD4^+T$ cells and the $CD8^+T$ cells obtained by magnetic-activated cell sorting were about 92.4% and 90.7%, respectively.

4.3 Preparation of sdCAR-T Cells by Electrotransfection

This example used a φC31 site-specific integrase system to insert the genes expressing the dual chimeric antigen receptor into genome of T lymphocyte to prepare sdCAR-T cells safely and efficiently. The φC31 integrase-mediated recombination system belongs to highly conservative serine recombinase. Its near N terminal is an active region containing a serine residue. The serine residue attacks the DNA skeleton for staggered cut to form a double-stranded broken terminal of 3-OH, while the 5-phosphate group is covalently linked with recombinase to form a cross-linked intermediate, finally realizing gene recombination. Compared with lentivirus and a transposon system, the recombination system can integrate large fragments of exogenous genes safely, efficiently and accurately. The φC31 integrase-mediated recombination system has the advantages of unidirectional integration and no need of external cofactors, and can realize stable and efficient expression of exogenous genes. In order to further improve the integration efficiency and specificity, the weight ratio of the integrase plasmids to the overexpression vector plasmids in the mixed plasmid was adjusted to 50:1 during electrotransfection. The electrotransfection operation was performed using Lonza Corporation's electrotransfection instruments and electrotransfection kits. Specific implementation steps of electrotransfection:

1) CD3$^+$T cells were inoculated into a complete culture medium (RPMI1640, 10% FBS), the cell density was controlled at 5×10$^5$ cells/mL, and growth factor IL-2 was added to the final concentration of 50 U/mL respectively, and cultured at 37° C. with 5% CO$_2$ for 48 h.

2) After the cultivation was finished, the cells were counted. The culture solution with a total cell number of 5×10$^6$ was sucked, and centrifuged at a centrifugal force of 200 g at room temperature for 10 min, the supernatant was discarded. The cells were resuspended with 100 μL of 4D-Nucleofector electrotransfection solution.

3) 2 μg of plasmid mixture (including 1.96 μg of φC31 integrase plasmid and 0.04 μg of overexpression vector) was added and fully and evenly mixed. The mixed electrotransfection mixture was transferred to a special electrotransfection cuvette, and F1-115 program was selected for electrotransfection.

4) After electrotransfection, 500 μL of complete culture medium containing IL-2 (RPMI1640, 10% FBS) was added, and turned upside down 2-3 times for uniform mixing. The evenly-mixed cell suspension was transferred to a new 12-well plate and 1.5 mL of complete culture medium was added.

5) After cultivation for 6 h, the culture plate was centrifuged at a centrifugal force of 140 g for 8 min, the supernatant was discarded and fresh preheated complete culture medium (RPMI1640, 10% FBS) containing IL-2 with a final concentration of 50 U/mL was added.

6) After cultivation again for 42 h, the culture plate was centrifuged at a centrifugal force of 300 g for 5 min, the supernatant was discarded, and fresh complete culture medium (containing IL-2 with a concentration of 50 U/mL) was added for cultivation.

Figure 7:
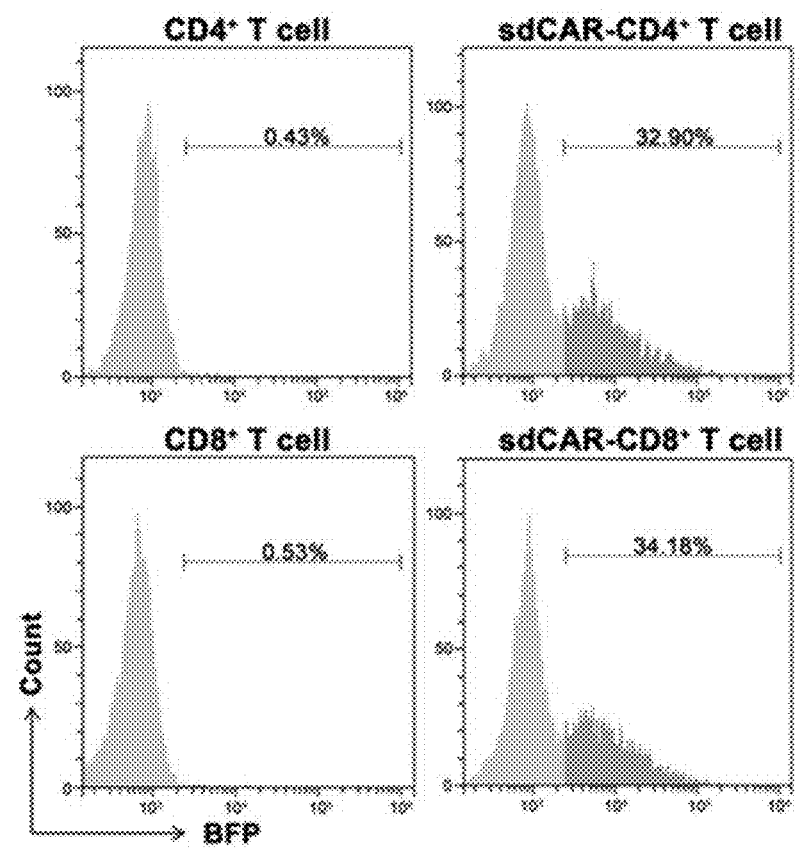
FIG. 7 is a flow cytometry diagram of sdCAR expression after electrotransfection of CD4$^+$T cells and CD8$^+$T cells.

SdCAR-T cells recombined BFP fluorescent tags. Therefore, the sdCAR transfection rates of CD4$^+$T cells and CD8$^+$T cells could be detected by flow cytometry respectively. The detection results are shown in FIG. 7. The results showed that the transfection positive rate of CD4$^+$T cells was 32.9%, and the positive rate of CD8$^+$T cells was 34.18%.

EXAMPLE 5

Optimization of the sdCAR Structure

This example described in detail different sdCAR-T cells obtained due to different structures of an extracellular hinge region and a transmembrane region, and used in vitro activation experiment to select the best structure. The detection index was CD69, an activation marker molecule produced on the surface of T cells. In this experiment, the selected target cell was the MSLN positive K562 tumor cell constructed in Example 3.6, and the added switching molecule was FITC. According to the different structures of sdCAR, the sdCAR-T cells were divided into 6 groups. The specific implementation solution is as follows:

group 1: the hinge region is CH2-CH3 sequence of IgG1, the transmembrane region is CD3 sequence, and this sdCAR-T cell is marked as CH2-CH3-3T cell;

group 2: the hinge region is CH2-CH3 sequence of IgG1, the transmembrane region is CD8 sequence, and this sdCAR-T cell is marked as CH2-CH3-8T cell;

group 3: the hinge region is CH2-CH3 sequence of IgG1, the transmembrane region is CD28 sequence, and this sdCAR-T cell is marked as CH2-CH3-28T cell;

group 4: the hinge region is human CD8α sequence, the transmembrane region is CD3 sequence, and this sdCAR-T cell is marked as CD8α-3T cell;

group 5: the hinge region is human CD8α sequence, the transmembrane region is CD8 sequence, and this sdCAR-T cell is marked as CD8α-8T cell; and group 6: the hinge region is human CD8α sequence, the transmembrane region is CD28 sequence, and this sdCAR-T cell is marked as CD8α-28T cell.

Implementation steps are as follows.

1) Effector cells and target cells were plated at a ratio of 1:2, and a switching molecule FITC was added to a final concentration of 100 pM.

2) Gibberellic acid acetoxymethyl ester was added respectively for culturing overnight (8 h), and centrifuged at a centrifugal force of 800 g for 5 min, then the cells were collected.

3) The collected cells were directly labelled with flow antibody CD69, and flow cytometry was performed on activated T cells.

Figure 8:
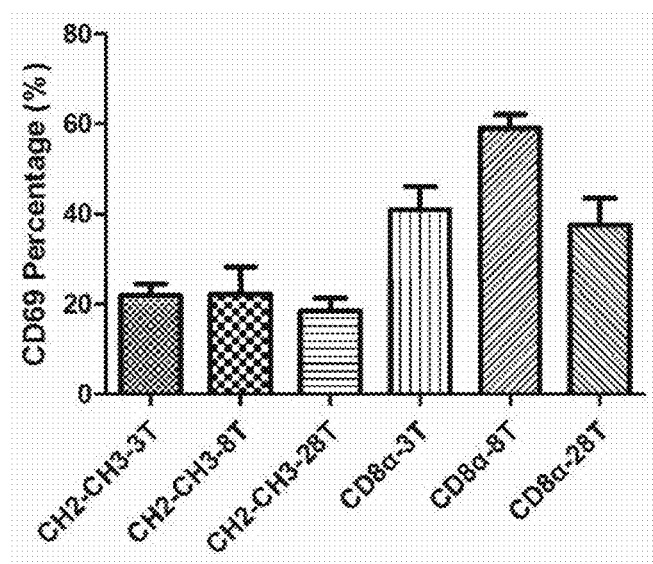
FIG. 8 is a comparison between in vitro activities of sdCAR-T cells with various structures.

The CD69 test results are shown in FIG. 8. The results showed that the level of CD69 expression obtained by sdCAR-T cells with the hinge region having CD8α sequence was much higher than that obtained by sdCAR-T cells with the hinge region having CH2-CH3 sequence, which indicated that the activity obtained by the sdCAR-T cells using the CD8α sequence was higher than that obtained using the CH2-CH3 sequence. The reason may be that the CD8α sequence has higher extracellular flexibility than the CH2-CH3 sequence and the obtained sdCAR receptor has higher flexibility. In addition, it is also found that the activity of sdCAR-T cells obtained by using a CD8 transmembrane region is higher than that obtained by using other types of transmembrane regions, which may be the result of the combined action of the CD8 transmembrane region and the extracellular CD8α hinge region. In summary, in order to obtain sdCAR-T cells with the best activity, the hinge region is selected to be the CD8α sequence, and the transmembrane region is selected to be the CD8 transmembrane region.

EXAMPLE 6

The Activation Test of sdCAR-T Cells In Vitro

Figure 2:
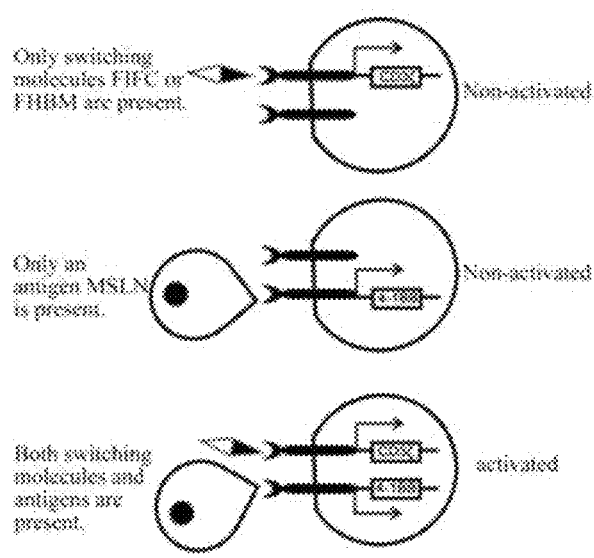
FIG. 2 is a schematic diagram of activation principle of sdCAR-T cells.

This example described in detail the research on the activation test of sdCAR-T cells in vitro. FIG. 2 is a schematic diagram of the activation principle of sdCAR-T cells. The dection indexes were the number of activation molecules CD69 on the surface of T cell and the levels of cytokines IL-2 and IFNγ produced during activation. In this test, the selected target cell was the MSLN positive K562 tumor cell constructed in Example 3.6. A total of four groups were designed (three parallel wells were designed for each group). The specific solution is as follows:

group 1: effector cells are sdCAR-T cells, target cells are MSLN positive K562 cells (MSLN$^+$K562), and no small molecule drugs are added;

group 2: effector cells are sdCAR-T cells, target cells are MSLN positive K562 cells (MSLN$^+$K562), and small molecule drug HM-3 is added;

group 3: effector cells are sdCAR-T cells, target cells are MSLN positive K562 cells (MSLN$^+$K562), and small molecule drug FITC is added; and group 4: effector cells are sdCAR-T cells, target cells are MSLN positive K562 cells (MSLN$^+$K562), and small molecule drug FHBM is added.

Implementation steps are as follows.

1) Effector cells and target cells were resuscitated respectively, and RPMI1640 culture medium was selected for culturing for 24 h. Effector cells and target cells were plated at a ratio of 1:2, and a corresponding switching molecule substance was added to a final concentration of 100 pM.

2) Gibberellic acid acetoxymethyl ester was respectively added for culturing overnight (8 h), centrifuged at a centrifugal force of 800 g for 5 min, and the cells and supernatant were collected respectively.

3) The contents of IL-2 and IFNγ in the collected supernatant were measured by using an ELISA method respectively.

4) The collected cells were directly labelled with flow antibody CD69, and flow cytometry was performed to obtain the number of activated T cells.

Figure 9:
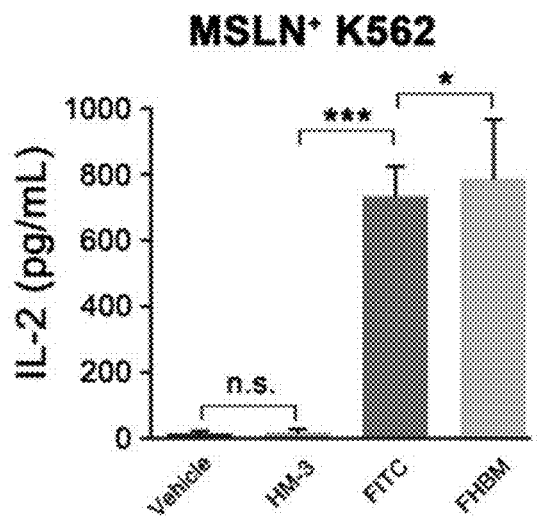
FIG. 9 is a diagram showing the level of IL-2 activated by sdCAR-T cells in vitro.
Figure 10:
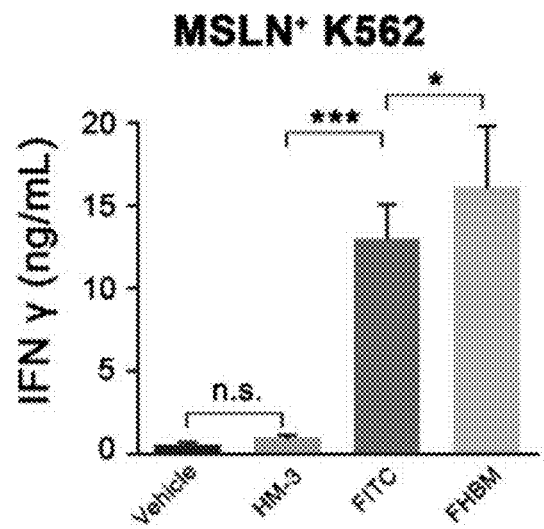
FIG. 10 is a diagram showing the level of IFNγ activated by sdCAR-T cells in vitro.

The test of the level of cytokine IL-2 in a cell supernatant is shown in FIG. 9, and the test of the level of cytokine IFNγ in the cell supernatant is shown in FIG. 10. Test results of cytokine IL-2 level: in the test group with the addition of exogenous bifunctional molecule FHBM, the IL-2 level was 789.67 pg/mL, and the IFNγ level was 16.13 ng/mL; in the test group with the addition of FITC, the IL-2 level was 734.67 pg/mL, and the IFNγ level was 13.00 ng/mL. The levels in the test results of the two groups were much higher than those in other test groups. This indicated that sdCAR-T cells can be activated persistently only when they recognized the tumor antigen MSLN and the exogenous switching molecules simultaneously.

Figure 11:
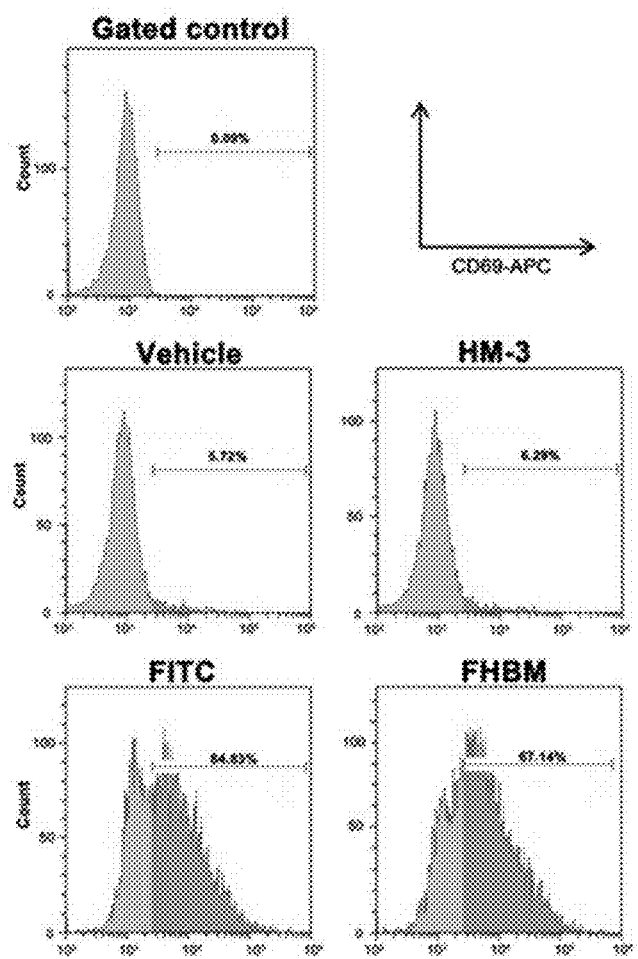
FIG. 11 is a flow cytometry diagram of CD69 on the surface of sdCAR-T cells.
Figure 12:
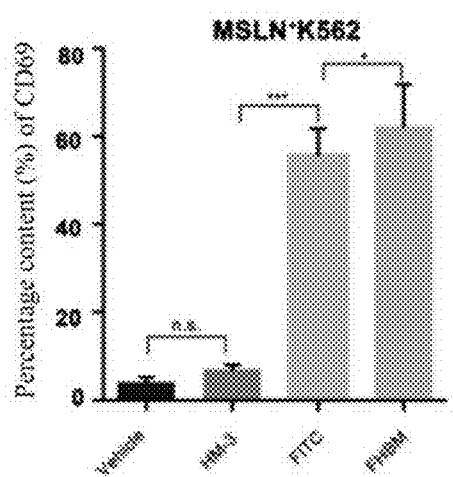
FIG. 12 is a diagram showing the analysis of CD69 expression on the surface of sdCAR-T cells.

The flow cytometry results of activator CD69 on the surface of sdCAR-T cells are shown in FIG. 11, and FIG. 12 is a corresponding result analysis graph. According to the analysis, the level of CD69 expression in sdCAR-T cells was about 55.67% under the condition of the tumor antigen MSLN and the exogenous molecule FITC. Under the condition of the tumor antigen MSLN and the exogenous bifunctional molecule FHBM, the level of CD69 expression was about 62.33%. Under the conditions of other groups, no significant expression of CD69 was observed, indicating that T cells were not activated, which was consistent with the release level of cytokines. In summary, the constructed sdCAR-T cells are only controlled by MSLN and exogenous switching molecule FITC (or FHBM), and this activation mode enhances the safety and controllability of CAR-T cells.

EXAMPLE 7

The Proliferation Test of sdCAR-T Cells In Vitro

This example described in detail the research on the proliferation test of sdCAR-T cells in vitro. The detection index was that the number of T cells changes over time. In this test, the selected target cell was the MSLN$^+$ K562 tumor cell constructed in Example 3.6. By adding different switching molecules, the effector cell sdCAR-T and the target cell MSLN$^+$K562 were co-incubated for 3 d, 4 d and 5 d. The design of the test group is the same as that of Example 5, with specific implementation steps as follows.

1) The target cell MSLN$^+$K562 was resuscitated, RPMI1640 culture medium was selected for culturing for 24 h and then treated with mitomycin C for 30 min, so that the target cell loses its proliferation ability.

2) Effector cells sdCAR-T cells were resuscitated, effector cells and target cells were plated at a ratio of 1:2, and the corresponding switching molecule was added to a final concentration of 100 pM.

3) At time points of the 3 d, 4 d and 5 d, the cells were collected respectively.

4) Flow cytometry was used to detect the percentage content of sdCAR-T cells at each time point and a cell counter was used to detect the total cell number at each time point.

5) The number of sdCAR-T cells at each time point was calculated.

Figure 13:
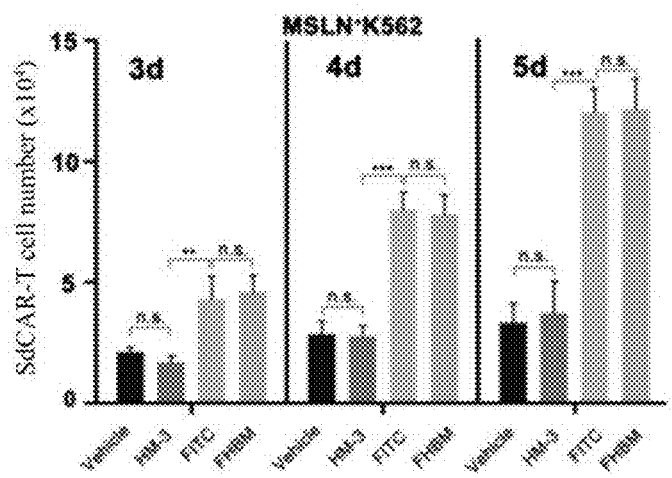
FIG. 13 is a diagram showing the detection of proliferation of sdCAR-T cells in vitro.

The cell proliferation results are shown in FIG. 13. Analysis showed that sdCAR-T cells could proliferate significantly only in the presence of the exogenous switching molecule FITC or FHBM and the tumor antigen MSLN. Therefore, the exogenous switching molecule can be used to regulate the activity of sdCAR-T cells, and precise regulation of the sdCAR-T cells can be realized through exogenous conditions.

EXAMPLE 8

The Cytotoxicity Test of sdCAR-T Cells In Vitro

This example verified the killing activity of the constructed sdCAR-T cells on tumor cells in vitro, and the selected target cells were MSLN single positive tumor cells and single positive tumor cells of negative control CEA. A total of four test groups were designed, each group had three parallel wells, and the design of the test group was the same as that of Example 6.

The cytotoxicity of sdCAR-T cells was determined according to the survival rate of target cells (MSLN$^+$K562). The selected target cells were equal mixed cells of MSLN and CEA. Because the constructed sdCAR-T cells had strong tumor specificity, CEA tumor cells were used as a negative control group, and the purpose of setting equal numbers of MSLN single positive cells and CEA single positive cells was to accurately and conveniently calculate the survival rate of MSLN tumor cells in each test group at each time. The survival rate of MSLN target cells in each test group was calculated according to the following formula, and then the tumor killing ability of the constructed CARs-T cells in vitro could be analyzed.

Survival rate of MSLN target cells =

$$\frac{\text{Proportion of MSLN target cells of the test group}}{\text{Proportion of CEA tumor cells of the test group}} \times 100\%$$

Specific implementation steps are as follows.

1) Effector cells and mixed target cells (MSLN$^+$K562:CEA$^+$K562, 1:1) were co-incubated at a ratio of 5:2 in a U-shaped 96-well plate, RPMI1640 (10% FBS) was selected as a co-culture medium, and corresponding switching molecule s were added.

2) Culturing at 37° C. for 22 h with 5% CO$_2$.

3) The ratio of MSLN and CEA tumor cells in each test group was detected by a flow cytometer, and then the survival rate of MSLN target cells was calculated.

Figure 14:
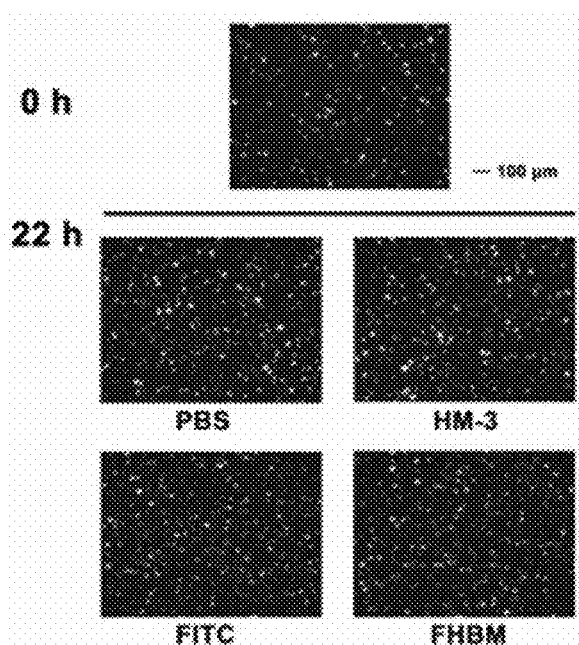
FIG. 14 is a diagram of fluorescence detection of cytotoxicity of sdCAR-T cells in vitro.
Figure 15:
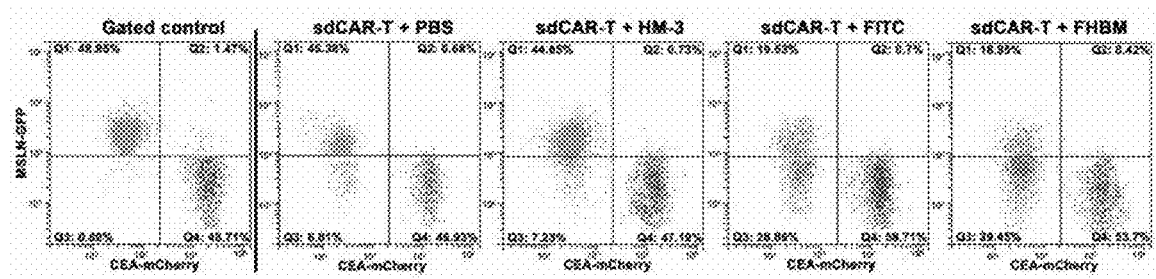
FIG. 15 is a flow cytometry diagram of cytotoxicity of sdCAR-T cells in vitro.
Figure 16:
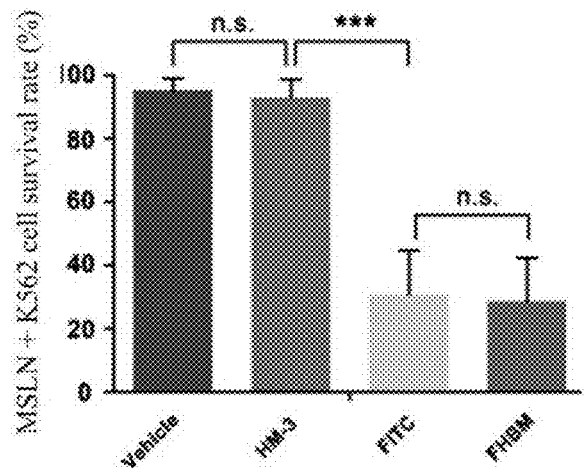
FIG. 16 is a diagram of cytotoxicity of sdCAR-T cells in vitro.

The fluorescence detection results of in vitro cytotoxicity of sdCAR-T cells are shown in FIG. 14. The fluorescence diagram shows that the percentage content of homologous target cells MSLN$^+$K562 (green fluorescence) in the FITC or FHBM molecular treatment group was significantly lower than that at the beginning of the test, indicating that sdCAR-T cells had higher cytotoxicity under these two conditions. Flow cytometry was used to quantitatively detect the cytotoxicity of sdCAR-T cells. See FIG. 15 for the test result graph. The cytotoxicity of sdCAR-T cells in each group could be calculated through the flow cytometry result. The results are shown in FIG. 16. The results showed that the survival rate of MSLN tumor cells in the FHBM test group was only 28.74%, while that in the FITC test group was about 30.98%, which was much lower than that in other test groups. In other test groups, the survival rate of MSLN tumor cells was about 100%, that is, sdCAR-T cells had no cytotoxicity. Therefore, only when two receptors of the constructed sdCAR-T cells are simultaneously targeted and recognized by MSLN and FITC can the sdCAR-T cells exert cytotoxicity to a large degree. Therefore, the use of the exogenous small molecule antigen can control the cytotoxicity of CARs-T cells and improve the safety of CAR-T cells.

EXAMPLE 9

Time Regulation of In Vitro Activity of sdCAR-T Cells by Exogenous Switching Molecules This example verified that the killing activity of the sdCAR-T cells on tumor cells was subjected to time regulation by the switching molecules, and the selected target cells were MSLN single positive tumor cells and single positive tumor cells of negative control CEA. In the 14-hour test, the cytotoxicity of sdCAR-T cells was tested in real time with and without switching molecules. A total of four test groups were designed, each group had three parallel wells, and the design of test group was the same as that of Example 6.

Specific implementation steps are as follows.

1) Effector cells and mixed target cells (MSLN$^+$K562:CEA$^+$K562, 1:1) were co-incubated at a ratio of 5:2 in a 6-well plate, RPMI1640 (containing 10% FBS) was selected as a co-culture medium, cultured at 37° C. with 5% CO$_2$.

2) 100 µL of cell suspension was taken every 2 h as the culturing begins at the 0 h.

3) Corresponding switching molecules were added at the 4 h.

4) Co-culturing for 10 h (that is, cell suspension was taken 6 times); after the culture, the ratio of MSLN and CEA tumor cells in each test group was detected by a flow cytometer, and then the survival rate of MSLN target cells was calculated.

Figure 17:
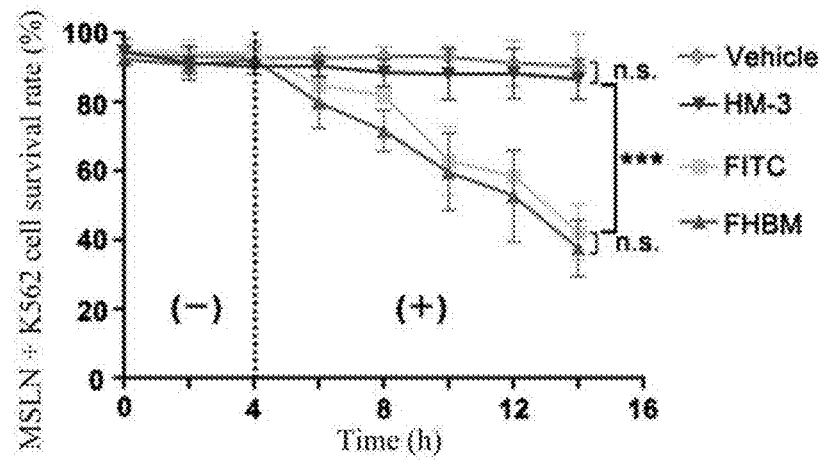
FIG. 17 is a detection diagram of time regulation of sdCAR-T cells by exogenous bifunctional switching molecules.

The in vitro cytotoxicity of sdCAR-T cells was subjected to time regulation by the exogenous switching molecules, with the test results shown in FIG. 17. The results showed that all groups showed no cytotoxicity without adding switching molecules. After corresponding switching molecules were added, only the FITC or FHBM treatment group had significant cytotoxicity, indicating that the exogenous switching molecules FITC and FHBM can effectively activate the cytotoxicity of sdCAR-T cells to MSLN$^+$K562 cells.

EXAMPLE 10

Concentration Regulation of In Vitro Activity of sdCAR-T Cells by Exogenous Switching Molecules This example verified that the killing activity of the sdCAR-T cells on tumor cells was subjected to concentration regulation by the switching molecules, and the selected target cells were MSLN single positive tumor cells and single positive tumor cells of negative control CEA. A total of 0, 0.5, 1, 5, 10, 50, 100, 500 and 1000 pM concentration gradients were designed in the test to detect the cytotoxicity of sdCAR-T cells in each group, with three parallel wells in each group.

Specific implementation steps are as follows.

1) Effector cells and mixed target cells (MSLN$^+$K562:CEA$^+$K562, 1:1) were co-incubated at a ratio of 5:2 in a U-shaped 96-well plate, and RPMI1640 (10% FBS) was selected as a co-culture medium.

2) Appropriate concentrations of switching molecules (FITC or FHBM) were added to the corresponding groups, and cultured at 37° C. with 5% CO$_2$ for 22 h.

3) After the culture was completed, the ratio of surviving MSLN and CEA tumor cells in each test group was detected by a flow cytometer, and then the survival rate of MSLN target cells was calculated.

Figure 18:
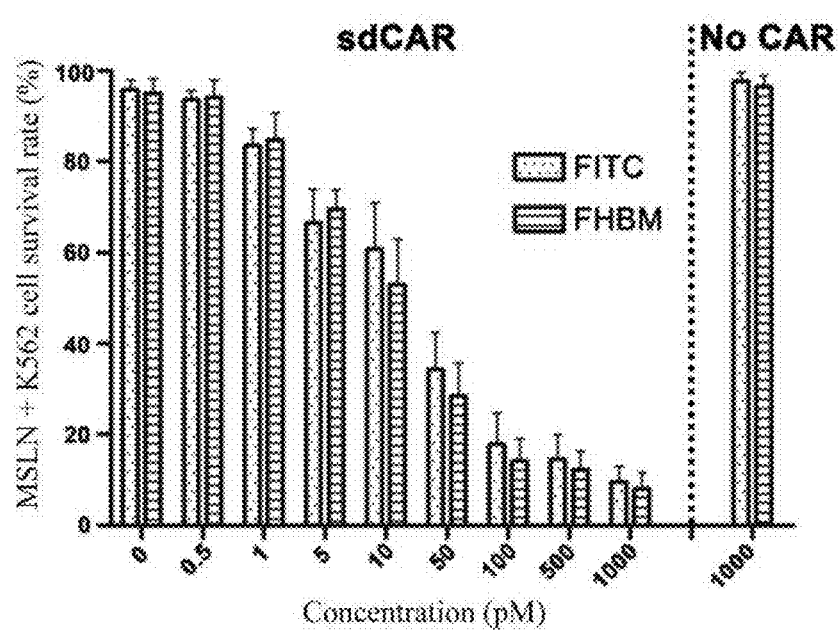
FIG. 18 is a detection diagram of concentration regulation of sdCAR-T cells by exogenous bifunctional switching molecules.

The in vitro cytotoxicity of sdCAR-T cells was subjected to concentration regulation by the exogenous switching molecules, with the test results shown in FIG. 18. The results showed that the cytotoxicity of sdCAR-T cells increased with the concentration when the switching molecule was at a low level (≤100 pM), but when the switching molecule reached a higher concentration level (>100 pM), the cytotoxicity was not proportional to the concentration of the switching molecules, and basically remains at the same level. This may be because the FITC receptor in the sdCAR structure had been recognized and saturated when the switching molecule was greater than 100 pM. Therefore, the activity of the constructed sdCAR-T cells depended strictly on the FITC or FHBM switching molecules. Exogenous small molecules not only can control the activity switching, but also can obtain different levels of cytotoxicity by different added concentrations. This provides a controllable approach for the safe clinical use of CAR-T cells to treat tumors.

EXAMPLE 11

The Tumor Killing Test by sdCAR-T Cells In Vivo

Figure 19:
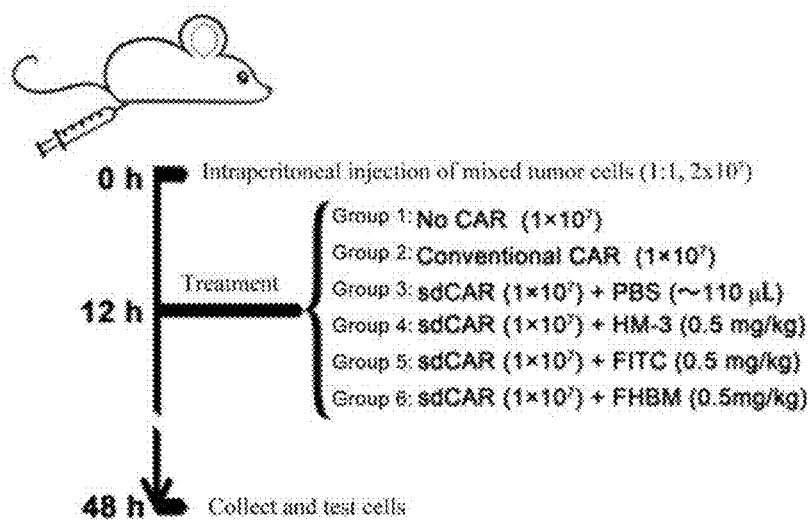
FIG. 19 is a flow chart of testing of sdCAR-T cells in vivo.

Female nude mice BALB/c which were 6-8 weeks old were selected, MSLN$^+$K562 cells and CEA$^+$K562 cells were mixed equally and injected intraperitoneally into the nude mice, and then corresponding effector cells and switching molecules were added respectively. Refer to FIG. 19 for details of the in vivo test process. Six test groups were designed, with 6 nude mice in each group. Specific solutions are as follows:

group 1: effector cells are T cells (No CAR) and no switching molecules are added;

group 2: effector cells are the second generation of CAR-T cells (Conventional CAR) specific to MSLN, and no switching molecules are added;

group 3: effector cells are sdCAR-T cells and no switching molecules are added;

group 4: effector cells are sdCAR-T cells, and small molecule HM-3 is added;

group 5: effector cells are sdCAR-T cells and switching molecule FITC is added; and group 6: effector cells are sdCAR-T cells, and switching molecule FHBM is added.

After the test was completed, the nude mice were euthanized, and then 5 mL of pre-cooled PBS was injected into the abdominal cavities of the nude mice. After the abdominal cavities of the nude mice were rubbed many times, the abdominal cavity fluid was sucked out completely, and centrifuged at a centrifugal force of 800 g for 8 min. The cells were collected, and the percentage of the two tumor cells was measured by flow cytometry, and then the in vivo activity of sdCAR-T cells could be calculated. In addition, the above centrifuged supernatant was collected to measure the release levels of cytokines IL-2 and IFNγ respectively.

Figure 20:
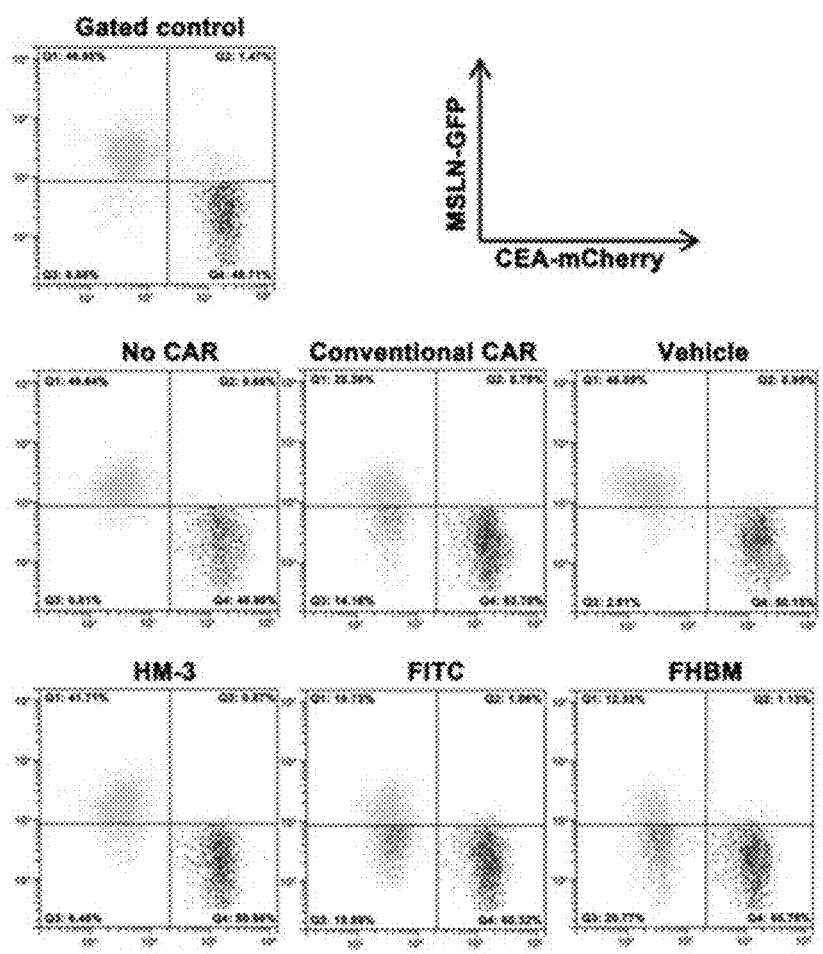
FIG. 20 is a flow cytometry diagram of cytotoxicity of sdCAR-T cells in vivo.
Figure 21:
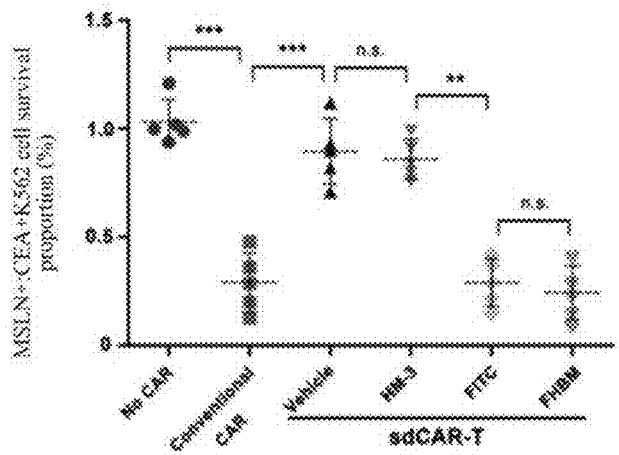
FIG. 21 is a diagram of cytotoxicity of sdCAR-T cells in vivo.

In vivo cytotoxicity of sdCAR-T cells was detected by flow cytometry, and the results are shown in FIG. 20. The cytotoxicity of sdCAR-T cells in each group could be calculated through the flow cytometry result. The results are shown in FIG. 21. The results showed that in the FITC or FHBM treatment group, sdCAR-T cells showed significant cytotoxicity, and the cytotoxicity level was similar to that of Conventional CAR-T cells. Meanwhile, it was observed that the cytotoxicity of the FHBM treatment group was better than that of the FITC treatment group. The reasons may be as follows: 1. HM-3, a component of the bifunctional molecule FHBM, has the function of inhibiting tumor development. 2. The FHBM targets both sdCAR-T cells and MSLN$^+$K562 tumor cells, which may shorten the effective distance between effector cells and target cells and increase the cytotoxicity of effector cells. In other test groups treated with other switching molecules, the obtained survival rate of MSLN tumor cells was similar to that of the group with no CAR-T cells, that is, sdCAR-T cells have no cytotoxicity. Therefore, in vivo, the cytotoxicity of sdCAR-T cells depends on the tumor antigen MSLN and the switching molecule FITC (or FHBM) to improve the safety of CAR-T cells.

Figure 22:
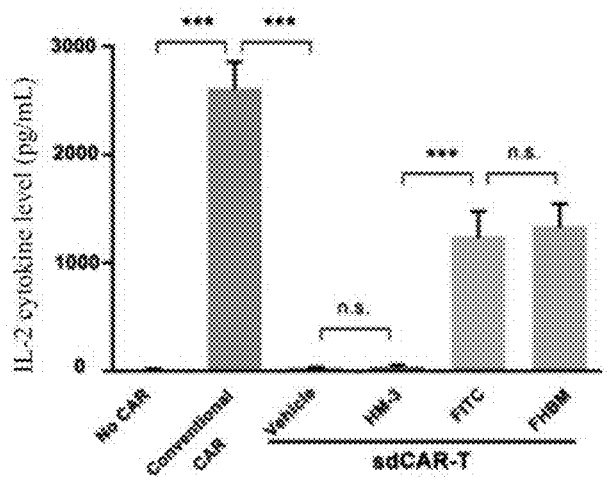
FIG. 22 is a diagram showing the level of IL-2 released by sdCAR-T cells in vivo.
Figure 23:
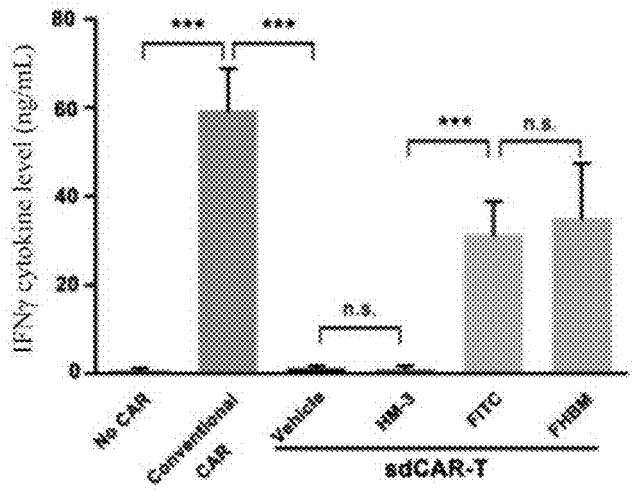
FIG. 23 is a diagram showing the level of IFNγ released by sdCAR-T cells in vivo.

The in vivo cytokine IL-2 release level is shown in FIG. 22, and the cytokine IFNγ release level is shown in FIG. 23. The trends of release levels of the two cytokines were basically the same. In the FITC or FHBM treatment group, sdCAR-T cells could release significant cytokine levels while effectively killing tumor cells. However, compared with the Conventional CAR-T cell group, the FITC or FHBM treatment group significantly reduced the release level (only half of the level), which indicates that when switching molecules and sdCAR-T cells were used to treat tumors, the level of the cytokine released was lower, and thus CRS toxicity could be effectively alleviated.

In summary, only when the constructed sdCAR-T cells simultaneously recognized the endogenous tumor cell antigen MSLN and the exogenous molecular switch FITC (or FHBM) in vivo, they could activate the cytotoxicity, thus exerting anti-tumor activity. In vivo tests confirmed that the design of the dual chimeric antigen receptor can enhance the tumor specificity of T cells and solve the toxicity of targeted non-tumor. At the same time, the dose of FITC (or FHBM) molecules added can be controlled to regulate the quantity of sdCAR-T cells activated, which can solve the existing treatment toxicity of cytokine storm and obviously improve the application safety.

EXAMPLE 12

Use of sdCAR-T Cells in Solid Tumors

Figure 24:
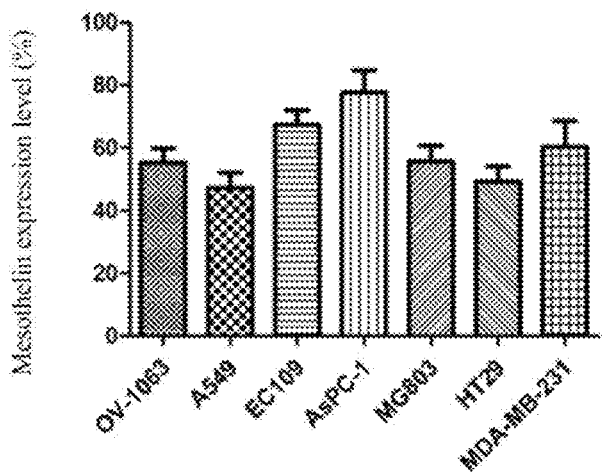
FIG. 24 is a diagram showing the level of mesothelin expressed by various solid tumors.
Figure 25:
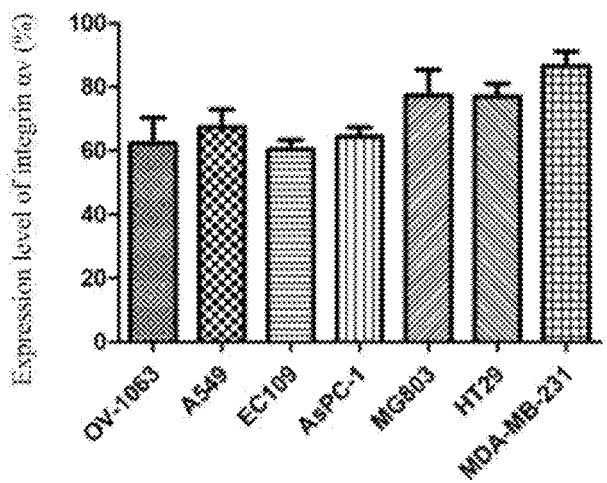
FIG. 25 is a diagram showing the level of integrin αv expressed by various solid tumors.
Figure 26:
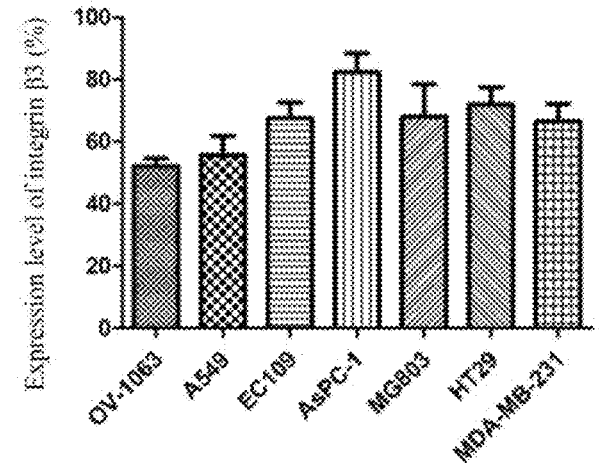
FIG. 26 is a diagram showing the level of integrin β3 expressed by various solid tumors.

According to the above results of in vitro and in vivo tests of sdCAR-T cells, in order to further verify the therapeutic effect on solid tumors, the selected solid tumors are highly expressed MSLN and integrin. The selected solid tumors mainly include ovarian cancer OV-1063, lung cancer A549, esophageal cancer EC109, pancreatic cancer AsPC-1, gastric cancer MG803, colorectal cancer HT29, breast cancer MDA-MB-231, liver cancer SMCC7721, melanoma Malme-3M, head and neck cancer CAL27, cervical cancer Hela and osteosarcoma U-2OS. The flow antibodies were used to detect the expression of MSLN on the surface of these solid tumor cells respectively. The test results are shown in FIG. 24. The results showed that the selected tumor cells all highly expressed the homologous tumor antigen MSLN, and the tumor antigen was specific to sdCAR-T cells. In addition, flow antibodies of integrins αv and β3 were used to detect the expression level of the integrins on the surface of the tumor cells respectively. The test results are shown in FIGS. 25 and 26. The test results showed that the selected tumor cells all highly expressed the integrins αα and β3. The above test results showed that various tumor cells were suitable for the sdCAR-T cells and the bifunctional molecule FHBM in the present invention.

Figure 27:
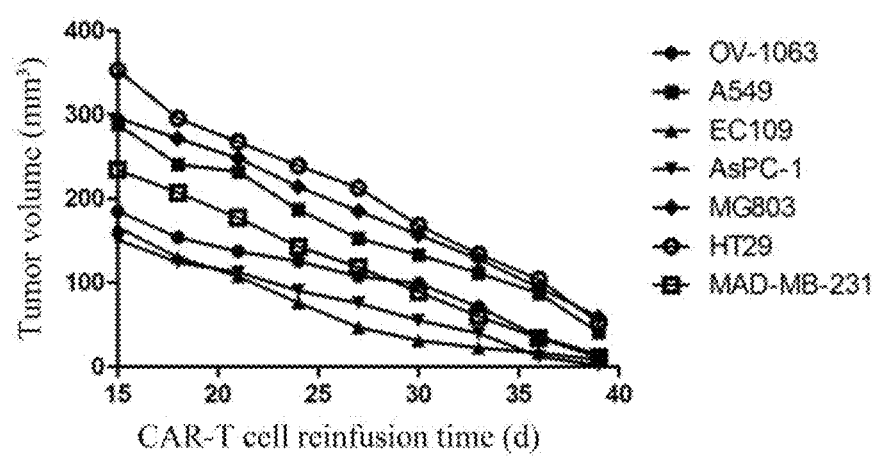
FIG. 27 is a diagram showing the level of cytotoxicity of sdCAR-T cells on solid tumors in vivo.

Female nude mice BALB/c, which were 6-8 weeks old, were selected and randomly divided into seven groups. The foregoing seven tumor cells ($1 \times 10^6$) were inoculated into the caudal vein respectively. The day when the tumor cells were inoculated was recorded as day 0, and the caudal vein reinfusion of $2 \times 10^6$ CAR-T cells and switching molecules FHBM was carried out on day 14. The detection scheme is as follows: the tumor volumes of nude mice in each group were measured every three days starting from day 15. The change trends of tumor volumes of various tumor cells with time are shown in FIG. 27. The results showed that the tumor volumes of the foregoing selected solid tumors were significantly reduced after reinfusion of sdCAR-T cells, indicating that sdCAR-T cells had high cytotoxicity to the foregoing solid tumors. Therefore, the combined cell immunotherapy (including the sdCAR-T cells and the bifunctional switching molecule FHBM) designed by the present invention has better cytotoxicity to tumor cells that highly express integrin αvβ3 and the MSLN antigen.

What is claimed is:

1. A switchable dual chimeric antigen receptor T cell, wherein the dual chimeric antigen receptor consists of a first chimeric antigen receptor for MSLN and a second chimeric antigen receptor for FITC; the dual chimeric antigen receptor contains a blue fluorescent protein tag downstream, and a linker peptide P2A is contained between the dual chimeric antigen receptor and the fluorescent protein tag;

wherein a molecular switch is provided in the form of FITC coupled to polypeptide HM-3, wherein the FITC and polypeptide HM-3 are coupled to form a bifunctional specific small molecule drug, and the amino acid sequence of the polypeptide HM-3 is Ile-Val-Arg-ArgAla-Asp-Arg-Ala-Ala-Val-Pro-Gly-Gly-Gly-Gly-Arg-Gly-Asp (SEQ ID NO: 18); and the nucleotide sequence of the dual chimeric antigen receptor as shown in SEQ ID NO: 1.

2. The switchable dual chimeric antigen receptor T cell and the molecular switch according to claim 1 for use in the field of preparing tumor drugs for treating overexpression of tumor antigen MSLN and integrin αvβ3.

3. The switchable dual chimeric antigen receptor T cell and the molecular switch according to claim 2 for use in the field of preparing tumor drugs for treating overexpression of tumor antigen MSLN and integrin αvβ3, wherein the tumors comprise ovarian cancer, lung cancer, esophageal cancer, pancreatic cancer, gastric cancer, colon cancer, breast cancer, liver cancer, melanoma, head and neck cancer, cervical cancer and osteosarcoma.

* * * * *